(12) United States Patent
Ichikawa et al.

(10) Patent No.: US 9,221,785 B2
(45) Date of Patent: Dec. 29, 2015

(54) SALT AND PHOTORESIST COMPOSITION CONTAINING THE SAME

(75) Inventors: Koji Ichikawa, Toyonaka (JP); Masako Sugihara, Nishinomiya (JP); Masahiko Shimada, Toyonaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 340 days.

(21) Appl. No.: 12/797,459

(22) Filed: Jun. 9, 2010

(65) Prior Publication Data
US 2010/0316951 A1 Dec. 16, 2010

(30) Foreign Application Priority Data

Jun. 12, 2009 (JP) .................. 2009-140957

(51) Int. Cl.
*G03F 7/004* (2006.01)
*G03F 7/38* (2006.01)
*C07D 317/12* (2006.01)
*C07D 317/16* (2006.01)
*C07D 317/24* (2006.01)
*C07D 319/02* (2006.01)
*C07D 319/12* (2006.01)
*C07D 321/02* (2006.01)
*C07D 327/04* (2006.01)
*C07D 327/06* (2006.01)
*C07D 339/02* (2006.01)
*C07D 339/06* (2006.01)
*C07D 339/08* (2006.01)
*C07C 381/12* (2006.01)
*C07C 309/17* (2006.01)
*G03F 7/039* (2006.01)

(52) U.S. Cl.
CPC ............ *C07D 327/06* (2013.01); *C07C 309/17* (2013.01); *C07C 381/12* (2013.01); *C07D 317/12* (2013.01); *C07D 317/16* (2013.01); *C07D 317/24* (2013.01); *C07D 319/12* (2013.01); *C07D 321/02* (2013.01); *C07D 327/04* (2013.01); *C07D 339/02* (2013.01); *C07D 339/06* (2013.01); *C07D 339/08* (2013.01); *G03F 7/0045* (2013.01); *G03F 7/0046* (2013.01); *G03F 7/0397* (2013.01); *C07C 2103/74* (2013.01); *G03F 7/38* (2013.01)

(58) Field of Classification Search
CPC ....... G03F 7/0045; G03F 7/30; C07D 339/02; C07D 339/06; C07D 339/08; C07D 319/12; C07D 317/12; C07D 317/16; C07D 317/24; C07D 321/02; C07D 327/04; C07D 327/06
USPC ........... 430/270.1, 326, 330, 921, 922; 549/9, 549/10, 11, 14, 20, 21, 30, 35, 36, 346, 347, 549/357, 377, 378, 380, 429, 430, 449, 455
See application file for complete search history.

(56) References Cited

U.S. PATENT DOCUMENTS

| | | | |
|---|---|---|---|
| 6,548,220 B2 * | 4/2003 | Uetani et al. ............... | 430/270.1 |
| 6,767,686 B2 * | 7/2004 | Uetani et al. ............... | 430/270.1 |
| 7,090,961 B2 * | 8/2006 | Kobayashi et al. ........ | 430/270.1 |
| 7,211,367 B2 * | 5/2007 | Kobayashi et al. ........ | 430/270.1 |
| 2002/0015913 A1 * | 2/2002 | Uetani et al. ............... | 430/270.1 |
| 2002/0146641 A1 * | 10/2002 | Uetani et al. ............... | 430/270.1 |
| 2003/0224290 A1 * | 12/2003 | Kobayashi et al. ........ | 430/270.1 |
| 2004/0224251 A1 * | 11/2004 | Toishi et al. ............... | 430/270.1 |
| 2006/0160023 A1 * | 7/2006 | Kobayashi et al. ........ | 430/270.1 |
| 2006/0194982 A1 | 8/2006 | Harada et al. | |
| 2008/0081925 A1 * | 4/2008 | Sakamoto et al. .............. | 558/52 |
| 2009/0131684 A1 * | 5/2009 | Kang et al. ...................... | 549/20 |
| 2010/0035180 A1 | 2/2010 | Shimada et al. | |
| 2010/0062365 A1 | 3/2010 | Shimada et al. | |

FOREIGN PATENT DOCUMENTS

| | | |
|---|---|---|
| JP | 11-52575 A | 2/1999 |
| JP | 2000-026446 A1 | 1/2000 |
| JP | 2008-013551 A | 1/2008 |
| JP | 2008-165218 A | 7/2008 |
| WO | WO 2008/099869 A1 | 8/2008 |

OTHER PUBLICATIONS

The Office Action (including an English translation), dated Jul. 4, 2014, issued in the corresponding Taiwanese Patent Application No. 099118806.

* cited by examiner

*Primary Examiner* — John S Chu
(74) *Attorney, Agent, or Firm* — Birch, Stewart, Kolasch & Birch, LLP

(57) ABSTRACT

A salt having a group represented by the formula (I):

$$-T \qquad (I)$$

wherein T represents a C3-C36 alicyclic hydrocarbon group in which at least two methylene groups are replaced by —O— or —S— and which can have one or more substituents.

6 Claims, No Drawings

SALT AND PHOTORESIST COMPOSITION CONTAINING THE SAME

This nonprovisional application claims priority under 35 U.S.C. §119(a) on Patent Application No. 2009-140957 filed in JAPAN on Jun. 12, 2009, the entire contents of which are hereby incorporated by reference.

FIELD OF THE INVENTION

The present invention relates to a salt suitable for an acid generator and a photoresist composition containing the same.

BACKGROUND OF THE INVENTION

A chemically amplified positive resist composition used for semiconductor microfabrication employing a lithography process contains an acid generator comprising a compound generating an acid by irradiation.

US 2006/0194982 A1 discloses triphenylsulfonium 1-(3-hydroxyadamantyl)methoxycarbonyldifluoromethanesulfonate and a photoresist composition comprising triphenylsulfonium 1-(3-hydroxyadamantyl)methoxycarbonyldifluoroethane as an acid generator.

SUMMARY OF THE INVENTION

An object of the present invention is to provide a novel salt suitable for an acid generator and a photoresist composition containing the same.

The present invention relates to the followings:

<1> A salt having a group represented by the formula (I):

-T                                            (I)

wherein T represents a C3-C36 alicyclic hydrocarbon group in which at least two methylene groups are replaced by —O— or —S— and which can have one or more substituents;

<2> The salt according to <1>, wherein the group represented by the formula (I) is a group represented by the formula (I-1):

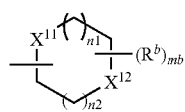
                                           (I-1)

wherein $X^{11}$ and $X^{12}$ independently each represent —O— or —S—, $R^b$ is independently in each occurrence a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, mb represents an integer of 0 to 4, n1 represents 1 or 2, and n2 represents 0 or 1;

<3> The salt according to <1> or <2>, wherein the group represented by the formula (I) is a group represented by the formula (I-2):

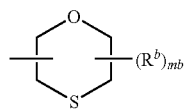
                                           (I-2)

wherein $R^b$ is independently in each occurrence a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, and mb represents an integer of 0 to 4;

<4> The salt according to any one of <1> to <3>, wherein the salt is represented by the formula (b1):

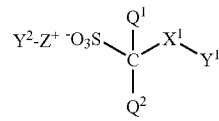
                                           (b1)

wherein $Q^1$ and $Q^2$ each independently represent a fluorine atom or a C1-C6 perfluoroalkyl group,
$X^1$ represents a C1-C17 saturated hydrocarbon group which can have one or more substituents, and one or more methylene groups in the saturated hydrocarbon group can be replaced by —O— or —CO—,
$Y^1$ represents a C3-C36 alicyclic hydrocarbon group, a C6-C24 aromatic hydrocarbon group or a group represented by the formula (I):

-T                                            (I)

wherein T represents a C3-C36 alicyclic hydrocarbon group in which at least two methylene groups are replaced by —O— or —S— and which can have one or more substituents, and the alicyclic hydrocarbon group and the aromatic hydrocarbon group can have one or more substituents, and one or more methylene groups in the alicyclic hydrocarbon group can be replaced by —O— or —CO—, with the proviso that the number of methylene groups in the alicyclic hydrocarbon group replaced by —O— is one,
Z represents an organic group and $Y^2$ represents a hydrogen atom or a group containing the group represented by the formula (I);

<5> A photoresist composition comprising the salt according to any one of <1> to <4> and a resin comprising a structural unit having an acid-labile group and being insoluble or poorly soluble in an aqueous alkali solution but becoming soluble in an aqueous alkali solution by the action of an acid;

<6> The photoresist composition according to <5>, wherein the photoresist composition further contains a basic compound;

<7> A process for producing a photoresist pattern comprising the following steps (1) to (5):

(1) a step of applying the photoresist composition according to <5> or <6> on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

DESCRIPTION OF PREFERRED EMBODIMENTS

The salt of the present invention has a group represented by the formula (I):

-T                                            (I)

wherein T represents a C3-C36 alicyclic hydrocarbon group in which at least two methylene groups are replaced by —O— or —S— and which can have one or more substituents.

Examples of the substituent in T include a halogen atom, a hydroxyl group, a carboxyl group, a C1-C12 aliphatic hydrocarbon group, a C3-C20 alicyclic hydrocarbon group, a C6-C20 aromatic hydrocarbon group, a C7-C21 aralkyl group, a glycidyloxy group and a C2-C4 acyl group.

Examples of the halogen atom include a fluorine atom, a bromine atom, a chlorine atom and an iodine atom. Examples of the C1-C12 aliphatic hydrocarbon group include a methy group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group and a heptadecyl group.

Examples of the C3-C20 alicyclic hydrocarbon group include a cyclohexyl group and an adamantyl group, and examples of the C6-C20 aromatic hydrocarbon group include a phenyl group, a naphthyl group, an anthryl group, a p-methylphenyl group, a p-tert-butylphenyl group, and a p-adamantylphenyl group. Examples of the C7-C21 aralkyl group include a benzyl group, a phenethyl group, a phenylpropyl group, a trityl group, a naphthylmethyl group and a naphthylethyl group. Examples of the C2-C4 acyl group include an acetyl group, a propionyl group and a butyryl group.

As the group represented by the formula (I), a group represented by the formula (I-1):

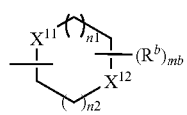

(I-1)

wherein $X^{11}$ and $X^{12}$ independently each represent —O— or —S—, $R^b$ is independently in each occurrence a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, mb represents an integer of 0 to 4, n1 represents 1 or 2, and n2 represents 0 or 1, is preferable.

Examples of the group represented by the formula (I) include the following groups represented by the formulae (T1) to (T7):

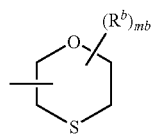

(T1)

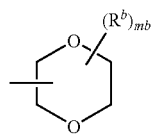

(T2)

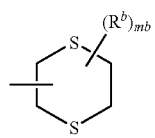

(T3)

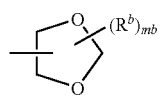

(T4)

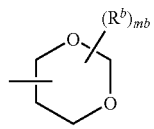

(T5)

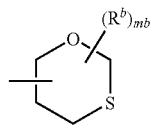

(T6)

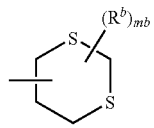

(T7)

As the group represented by the formula (I), a group represented by the formula (I-2):

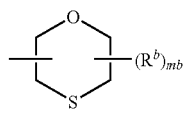

(I-2)

wherein $R^b$ is independently in each occurrence a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, and mb represents an integer of 0 to 4, is more preferable.

The salt of the present invention is preferably a salt represented by the formula (b1):

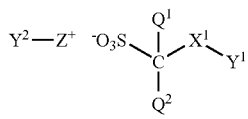

(b1)

wherein $Q^1$ and $Q^2$ each independently represent a fluorine atom or a C1-C6 perfluoroalkyl group, $X^1$ represents a C1-C17 saturated hydrocarbon group which can have one or more substituents, and one or more methylene groups in the saturated hydrocarbon group can be replaced by —O— or —CO—.

$Y^1$ represents a C3-C36 alicyclic hydrocarbon group, a C6-C24 aromatic hydrocarbon group or a group represented by the formula (I), and the alicyclic hydrocarbon group and the aromatic hydrocarbon group can have one or more substituents, and one or more methylene groups in the alicyclic hydrocarbon group can be replaced by —O— or —CO—, with the proviso that the number of methylene groups in the alicyclic hydrocarbon group replaced by —O— is one, Z represents an organic group and $Y^2$ represents a hydrogen atom or a group containing the group represented by the formula (I).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 saturated hydrocarbon group include a C1-C17 alkylene group and a divalent group having a cycloalkylene group. Examples of the alkylene group include a methylene group, an ethylene group, a trimethylene group, a tetramethylene group, a pentamethylene group, a hexamethylene group, a heptamethylene group, an octamethylene group, a nonamethylene group, a decamethylene group, an undecamethylene group, a dodecamethylene group, a tridecamethylene group, a tetradecamethylene group, a pentadecamethylene group, a hexadecamethylene group, a heptadecamethylene group, an isopropylene group, a sec-bytylene group and a tert-butylene group.

Examples of the divalent group having a cycloalkylene group include the following groups represented by the formulae ($X^1$-A) to ($X^1$-C):

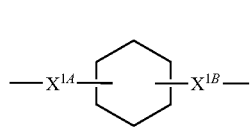
($X^1$-A)

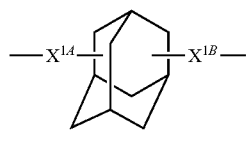
($X^1$-B)

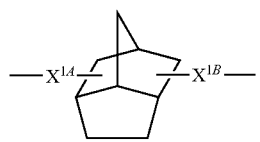
($X^1$-C)

wherein $X^{1A}$ and $X^{1B}$ independently each represent a C1-C6 alkylene group which can have one or more substituents, with the proviso that total carbon number of the group represented by the formula ($X^1$-A), ($X^1$-B) or ($X^1$-C) is 1 to 17.

One or more methylene groups in the C1-C17 saturated hydrocarbon group can be replaced by —O— or —CO—.

In the formula (b1), $X^1$ is preferably *—CO—O—$X^{a1}$— in which $X^{a1}$ represents a C1-C15 saturated hydrocarbon group which can have one or more substituents and one or more methylene groups in the saturated hydrocarbon group can be replaced by —O— or —CO—, and * represents a binding position to —$CQ^1Q^2$-.

$X^1$ is more preferably *—CO—O—$X^{a2}$—CO—O— in which $X^{a2}$ represents a C1-C13 saturated aliphatic hydrocarbon group which can have one or more substituents and one or more methylene groups in the saturated aliphatic hydrocarbon group can be replaced by —O— or —CO—, and * represents a binding position to —$CQ^1Q^2$-.

Examples of the substituent in $X^1$ include a halogen atom, a hydroxyl group, a carboxyl group, a C1-C12 aliphatic hydrocarbon group, a C3-C20 alicyclic hydrocarbon group, a C6-C20 aromatic hydrocarbon group, a C7-C21 aralkyl group, a glycidyloxy group and a C2-C4 acyl group. Examples of the halogen atom, the C1-C12 aliphatic hydrocarbon group, the C3-C20 alicyclic hydrocarbon group, the C6-C20 aromatic hydrocarbon group, the C7-C21 aralkyl group and the C2-C4 acyl group include the same as described above, respectively.

Specific examples of $X^1$ include the followings.

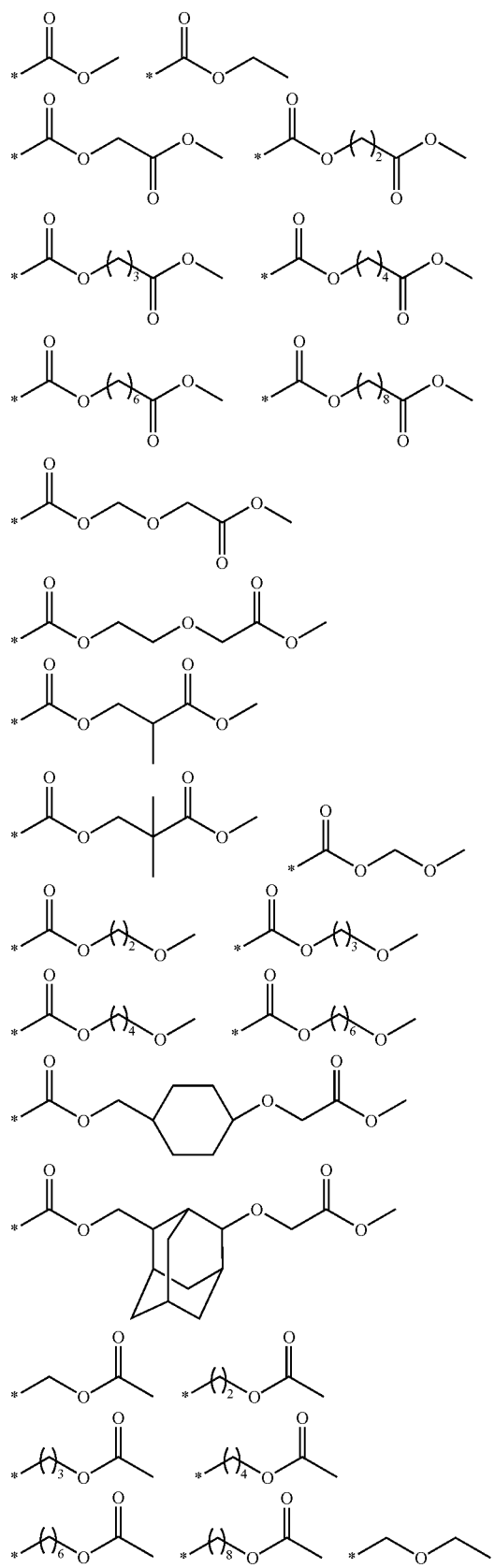

In the formula (b1), $Y^1$ represents a C3-C36 alicyclic hydrocarbon group, a C6-C24 aromatic hydrocarbon group or a group represented by the formula (I), and the alicyclic hydrocarbon group and the aromatic hydrocarbon group can have one or more substituents, and one or more methylene groups in the alicyclic hydrocarbon group can be replaced by —O— or —CO—, with the proviso that the number of methylene groups in the alicyclic hydrocarbon group replaced by —O— is one, Z represents an organic group and $Y^2$ represents a hydrogen atom or a group containing the group represented by the formula (I).

Examples of the substituent of the alicyclic hydrocarbon group and the aromatic hydrocarbon group include a halogen atom, a hydroxyl group, a C1-C12 aliphatic hydrocarbon group, a hydroxyl-containing C1-C12 aliphatic hydrocarbon group, a C3-C20 alicyclic hydrocarbon group, a C1-C12 alkoxy group, a C6-C20 aromatic hydrocarbon group, a C2-C21 aralkyl group, a C2-C4 acyl group, a glycidyloxy group, and a group represented by the formula: —(CH$_2$)$_{j2}$—O—CO—R$^{b1}$ wherein R$^{b1}$ represents a C1-C12 aliphatic hydrocarbon group, a C3-C20 alicyclic hydrocarbon group or a C6-C20 aromatic hydrocarbon group, and j2 represents an integer of 0 to 4. The aliphatic hydrocarbon group, the alicyclic hydrocarbon group, the C6-C20 aromatic hydrocarbon group and the aralkyl group, which are substituents of $Y^1$, can have one or more substituents such as an alkyl group, a halogen atom, a hydroxyl group and an oxo group.

Examples of the hydroxyl-containing C1-C12 aliphatic hydrocarbon group include a hydroxymethyl group and a hydroxyethyl group. Examples of the alicyclic hydrocarbon group in which one or more methylene groups are replaced by —O— or —CO— include a cyclic ether group, which is an alicyclic hydrocarbon group in which one methylene group is replaced by —O—, a saturated cyclic hydrocarbon group having an oxo group, which is an alicyclic hydrocarbon group in which one methylene group is replaced by —CO—, and a lactone group, which is an alicyclic hydrocarbon group in which neighboring two methylene groups are replaced by —O— and —CO, respectively. The number of methylene groups in the alicyclic hydrocarbon group replaced by —O— is one.

Examples the C3-C36 alicyclic hydrocarbon group and the C6-C24 aromatic hydrocarbon group include groups represented by the formulae (W1) to (W26):

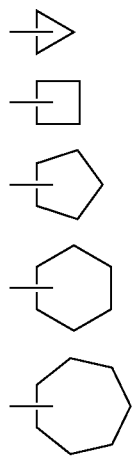

(W1)

(W2)

(W3)

(W4)

(W5)

(W6)

(W7)

(W8)

(W9)

(W10)

(W11)

(W12)

(W13)

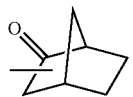

(W14)

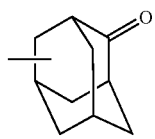

(W15)

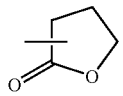

(W16)

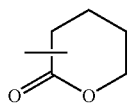

(W17)

-continued (W18) 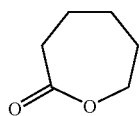

(W19) 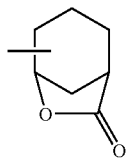

(W20) 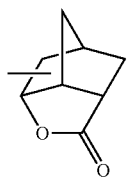

(W21) 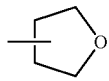

(W22) 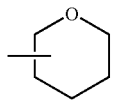

(W23) 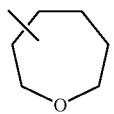

(W24) 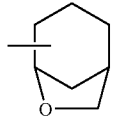

(W25) 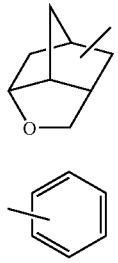

(W26) 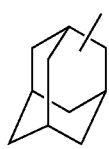

The above-mentioned groups represented by the formulae (W1) to (W26) can have one or more substituents. Among them, groups represented by the formula $(Y^1-1)$, $(Y^1-2)$, $(Y^1-3)$ and $(Y^1-4)$:

$(Y^1-1)$ 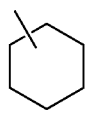

$(Y^1-2)$ 

$(Y^1-3)$ 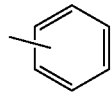

$(Y^1-4)$ wherein one or more methylene groups can be replaced by —O— or —CO— and one or more hydrogen atoms can be replaced by a substituent, are preferable.

Examples of $Y^1$ include the followings:

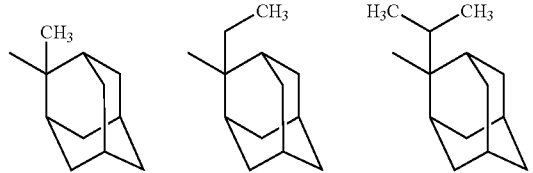
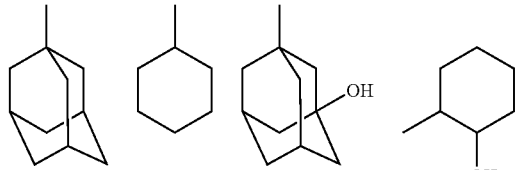
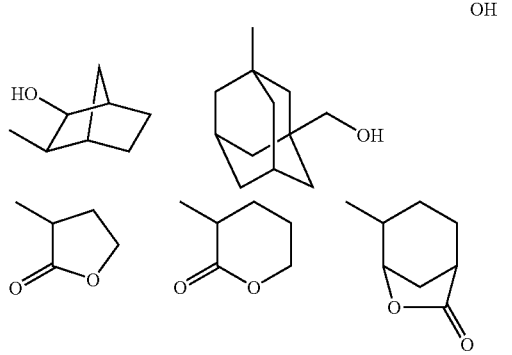
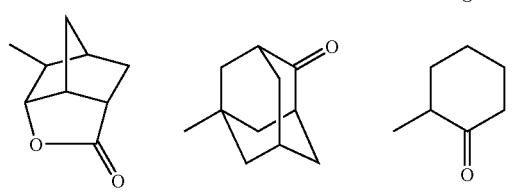
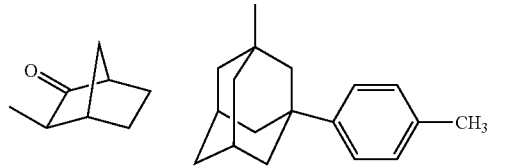

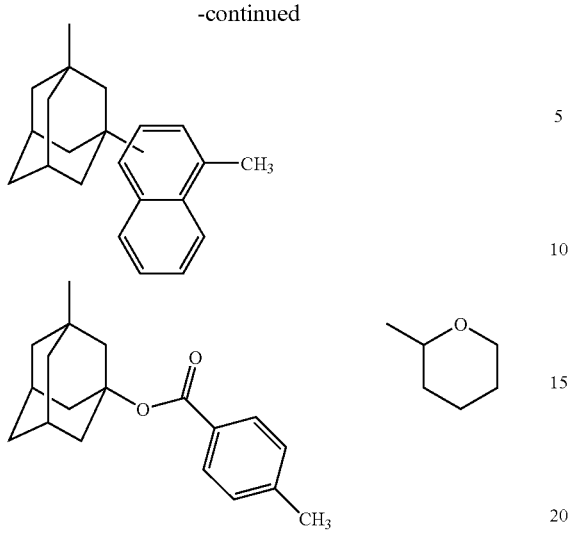

Examples of the anion part represented by the formula (c-1):

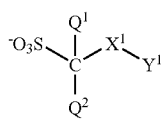
(c-1)

wherein $Q^1$, $Q^2$, $X^1$ and $Y^1$ are the same as defined above, of the salt represented by the formula (b1) include the followings:

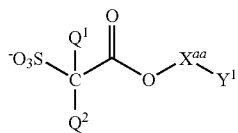
(c-a)

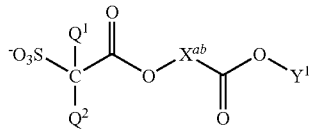
(c-b)

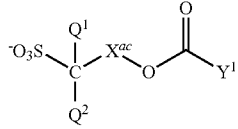
(c-c)

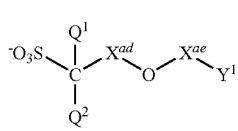
(c-d)

wherein $Q^1$, $Q^2$ and $Y^1$ are the same as defined above, and $X^{aa}$, $X^{ab}$, $X^{ac}$, $X^{ad}$ and $X^{ae}$ independently each represent a single bond or a C1-C15 alkylene group. Among them, the anion part represented by the formula (c-a) is preferable.

Examples of the anion part represented by the formula (c-a) include the followings.

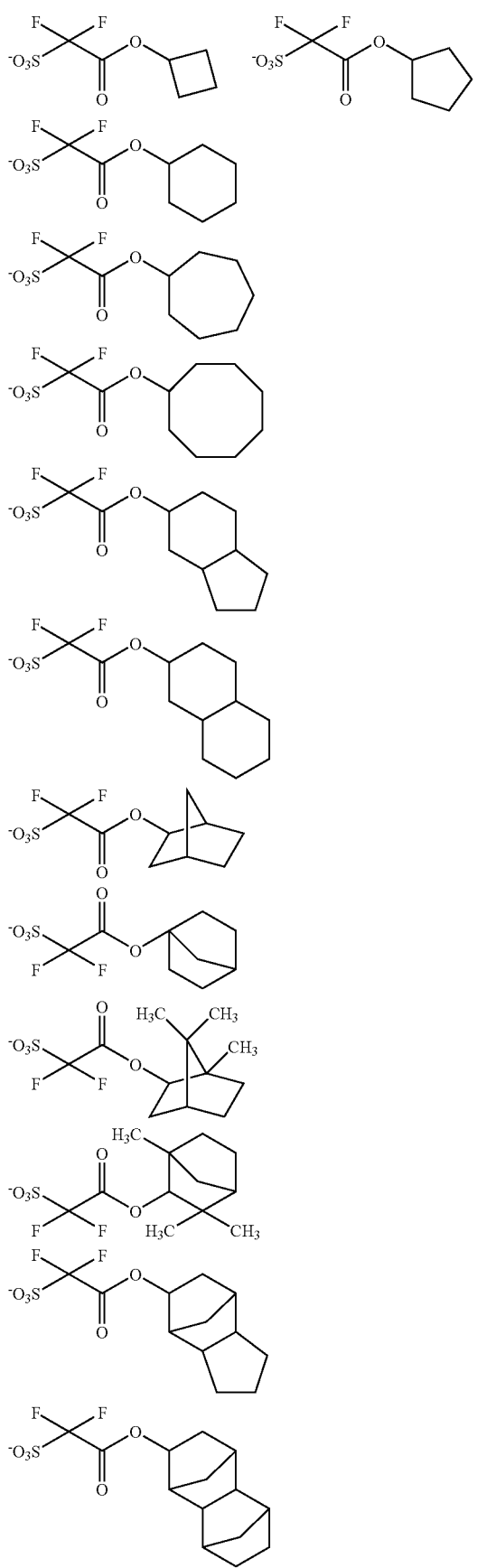

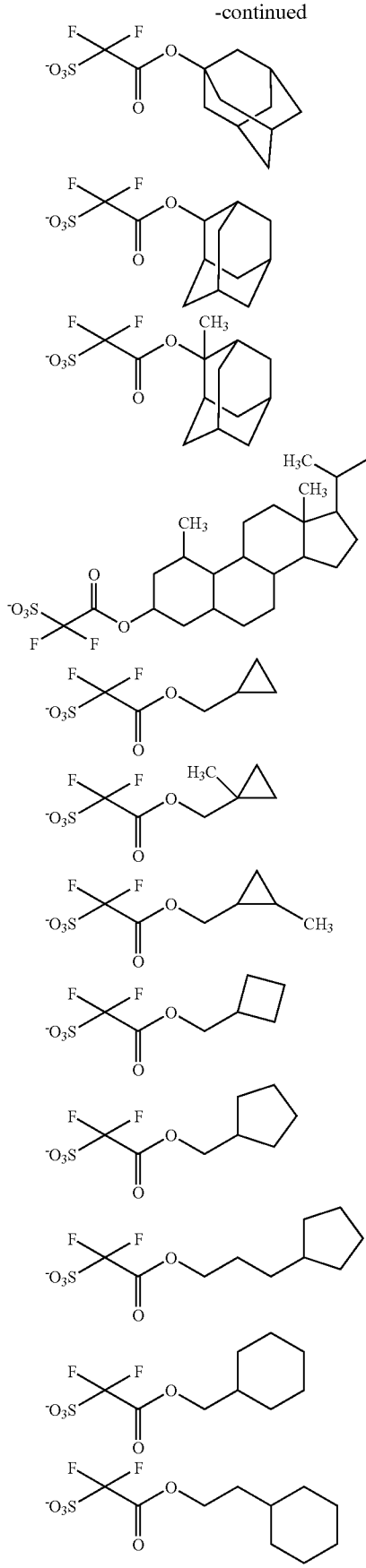

-continued
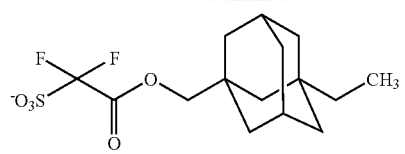
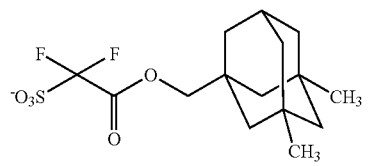
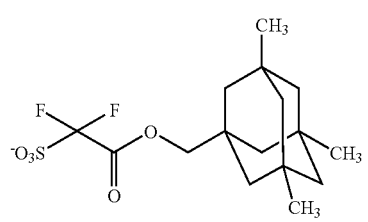
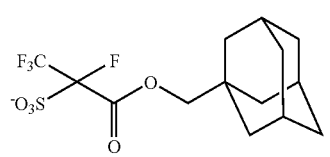
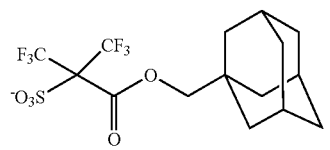
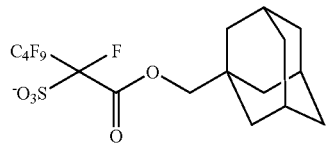
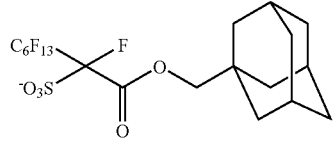
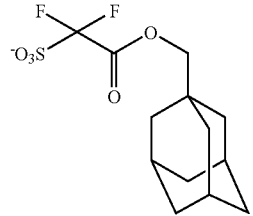
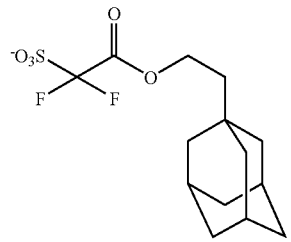
-continued
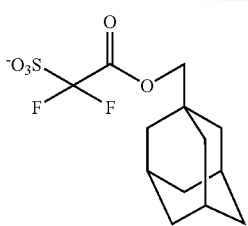
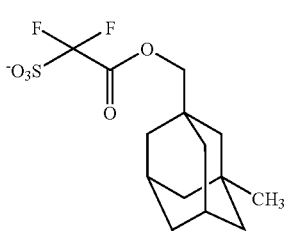
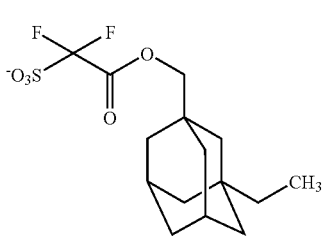
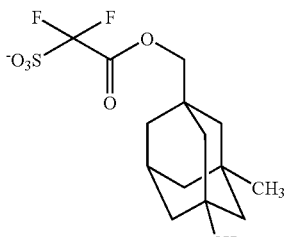
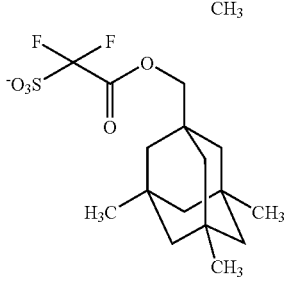
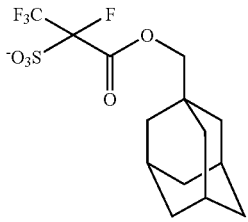
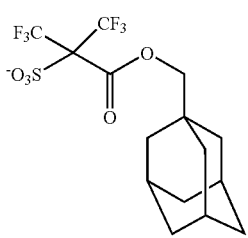

-continued
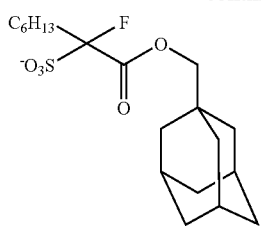
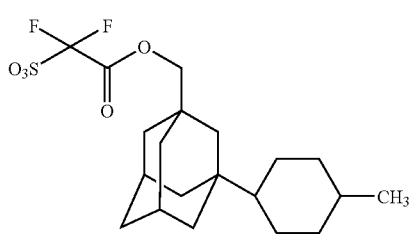
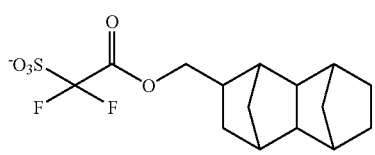
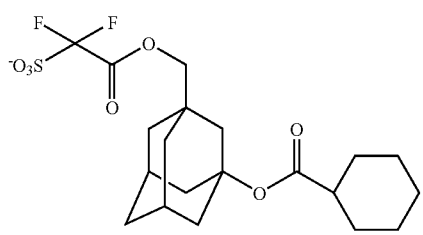
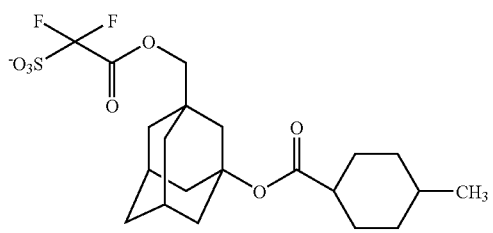
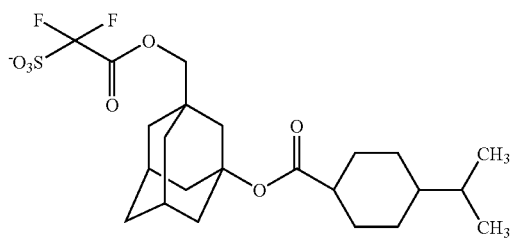
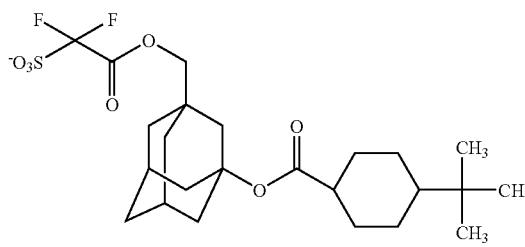
-continued
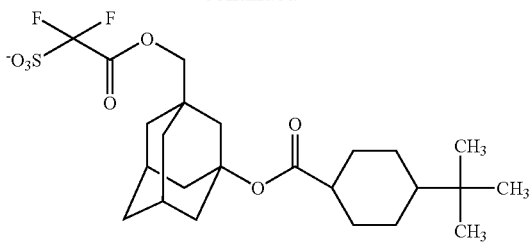
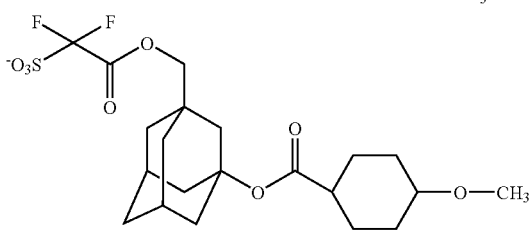
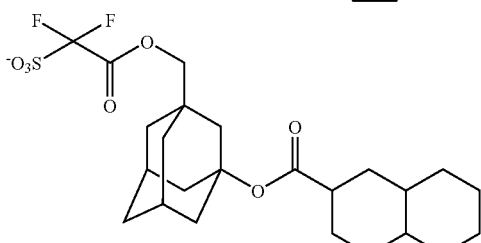
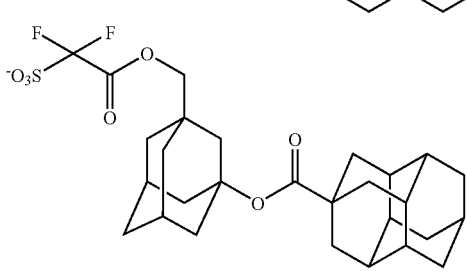
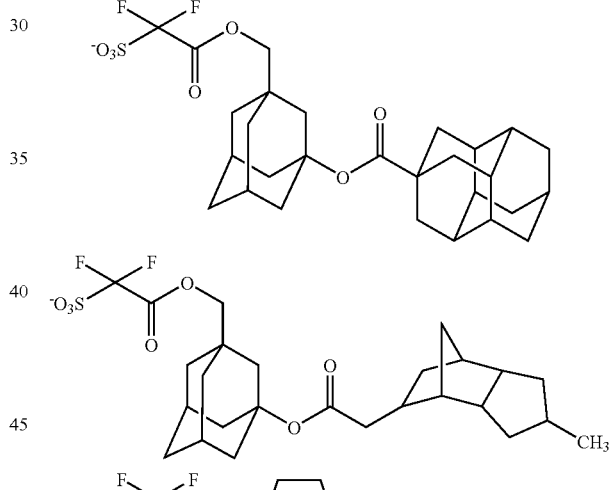
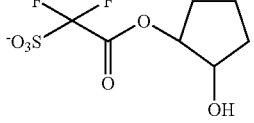
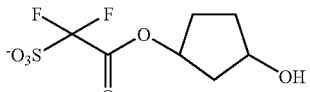
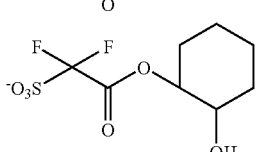
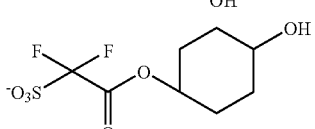

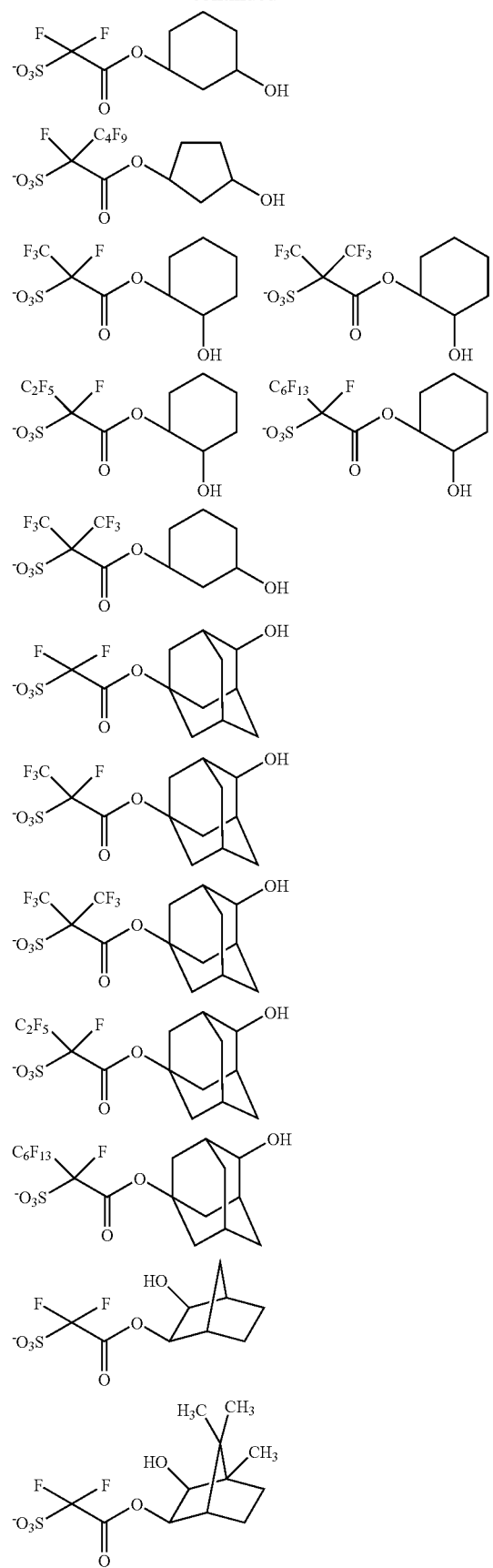
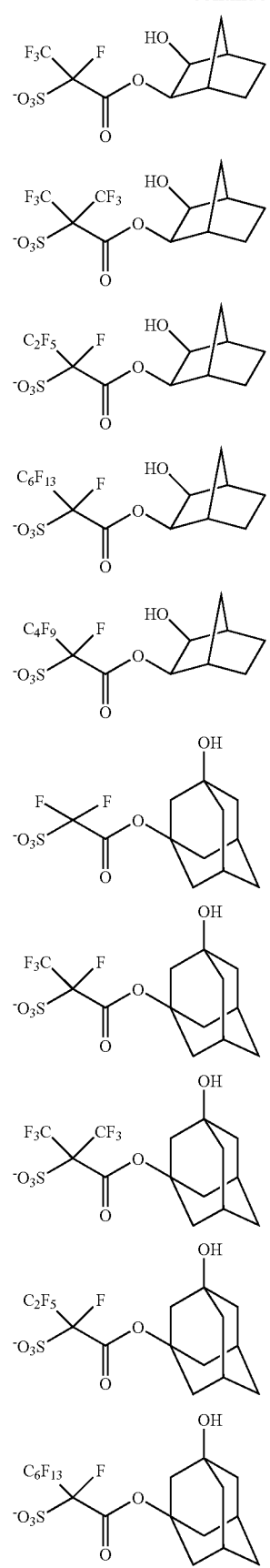

-continued
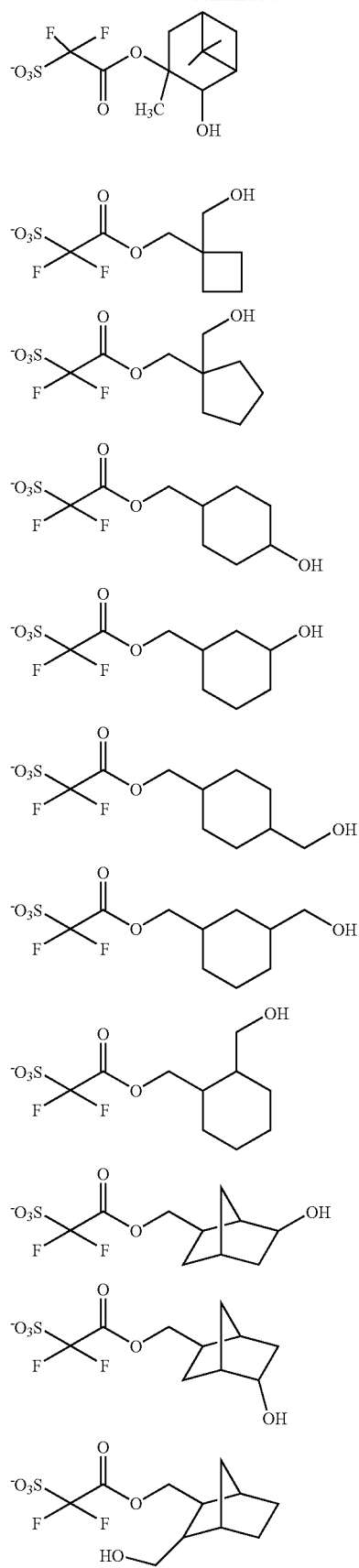
-continued
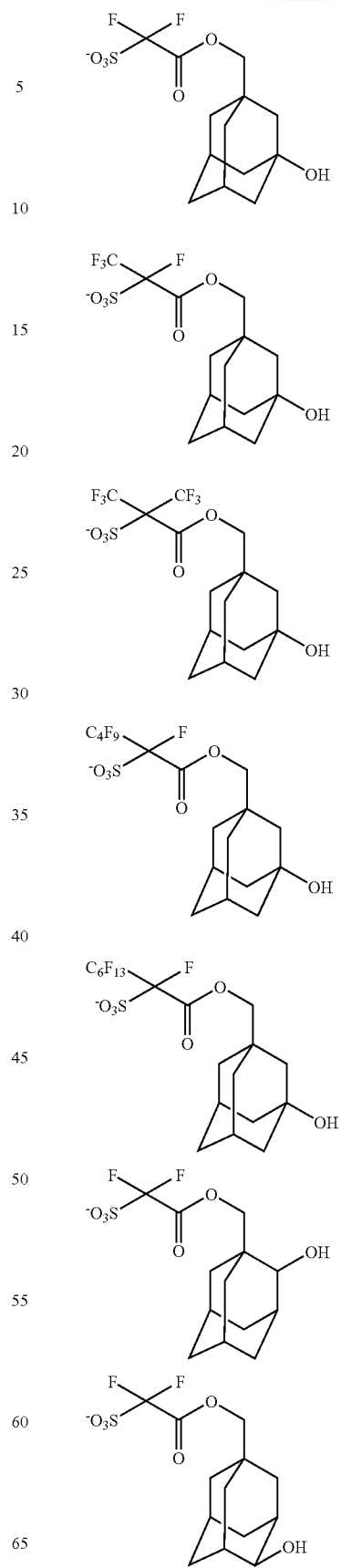

23
-continued
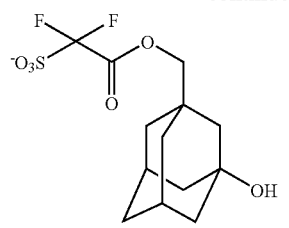
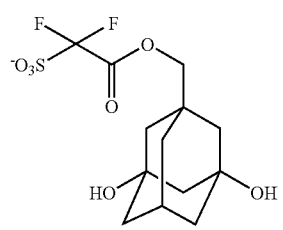
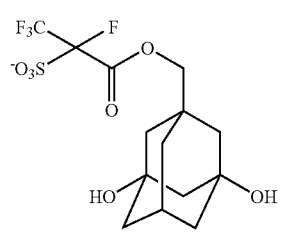
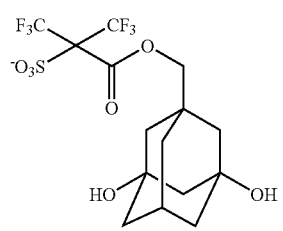
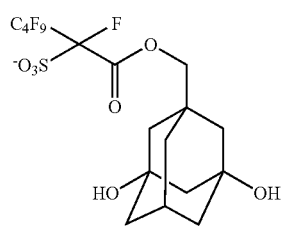
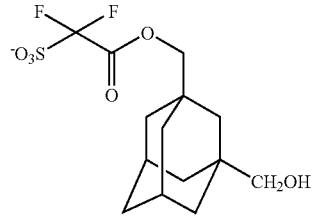
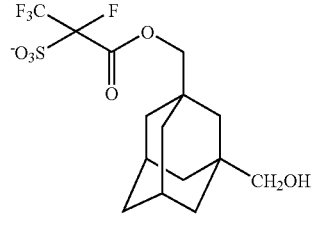
24
-continued
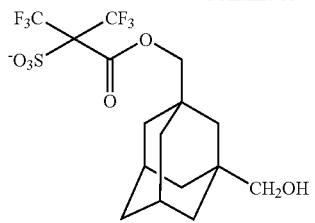
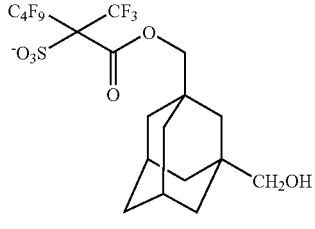
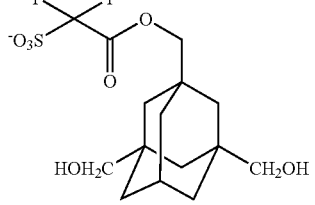
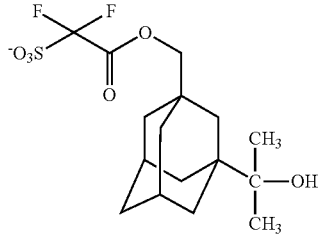
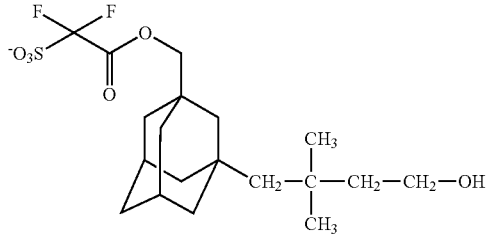
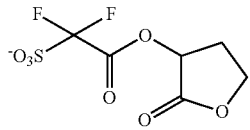
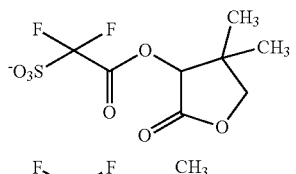
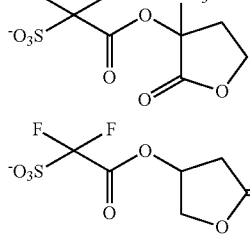

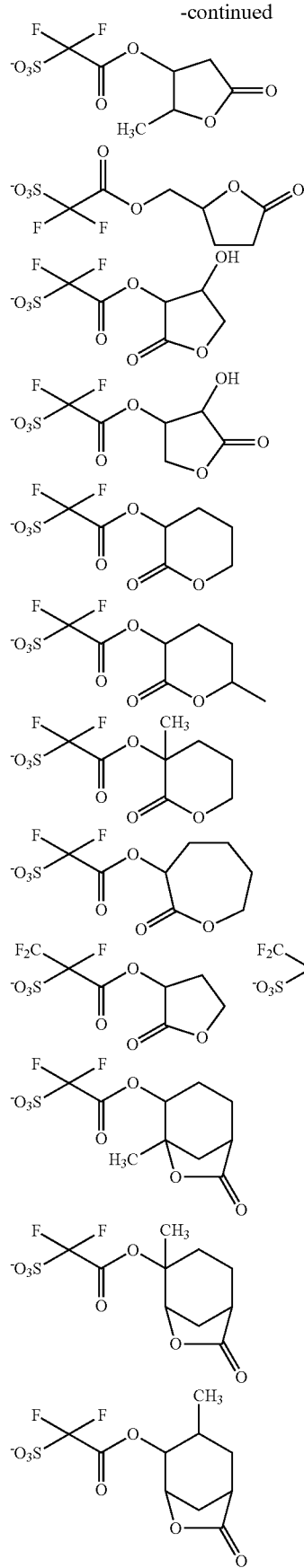
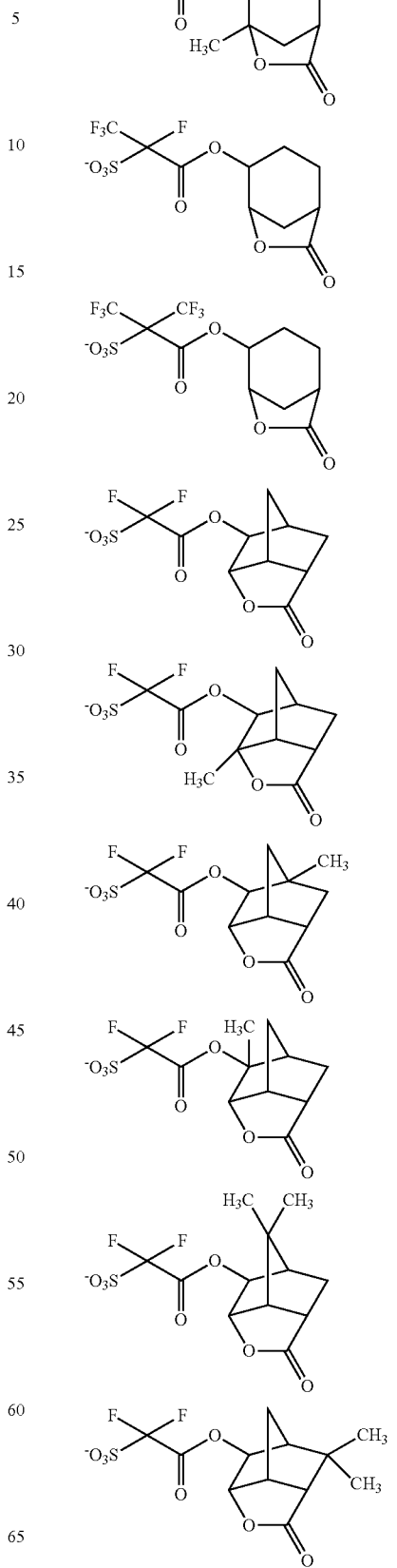

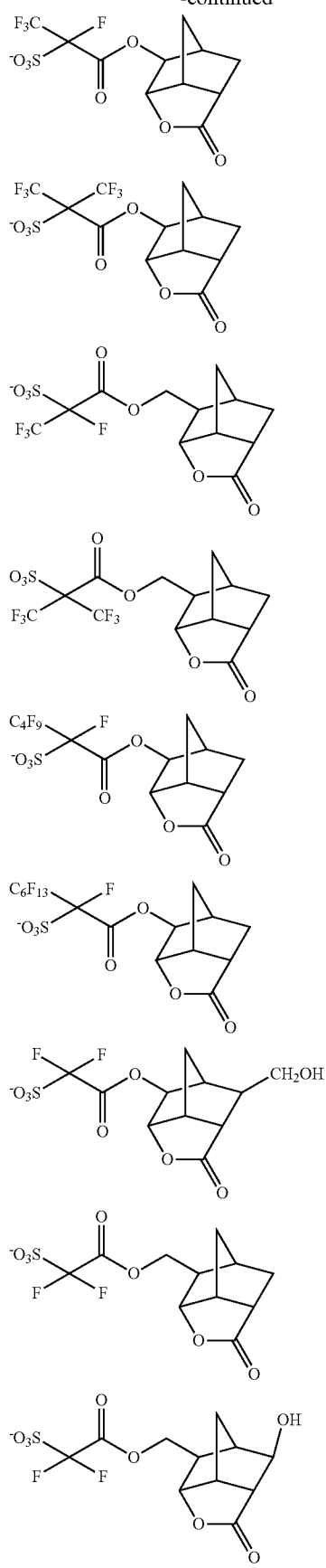
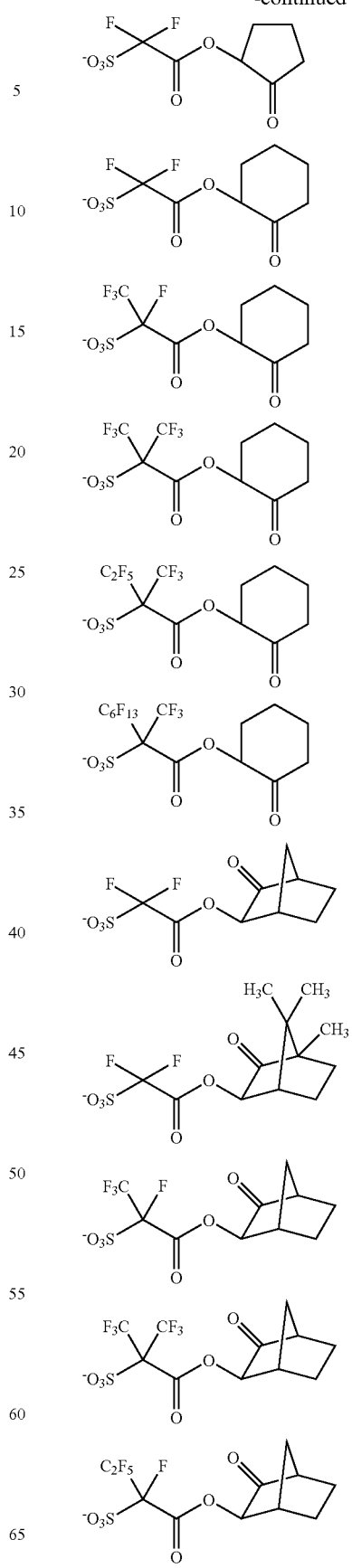

-continued
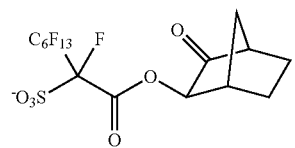
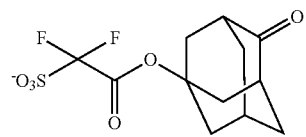
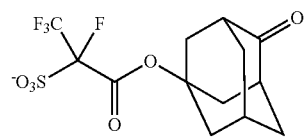
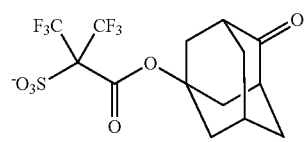
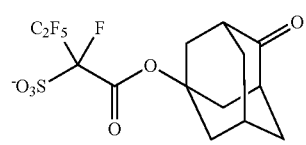
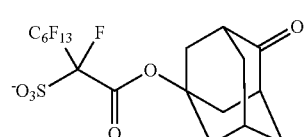
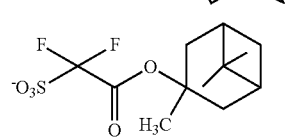
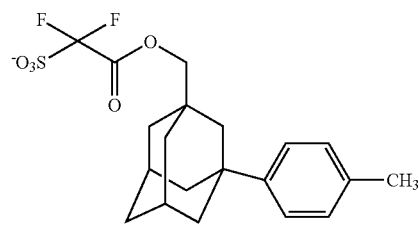
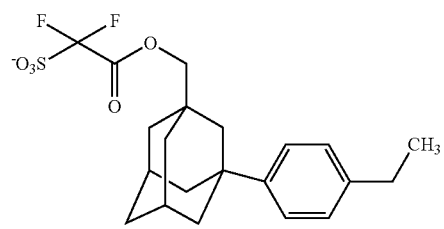
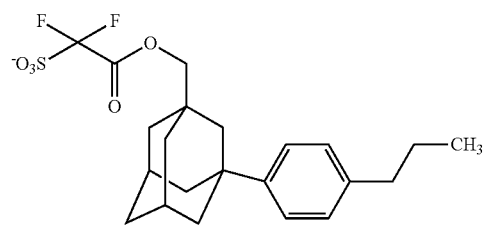
-continued
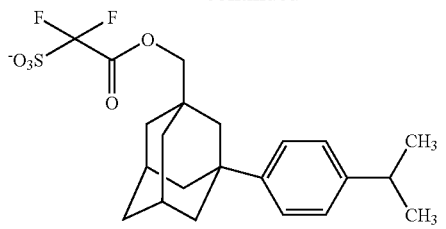
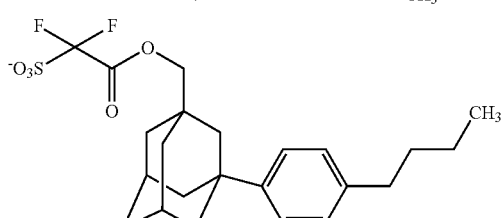
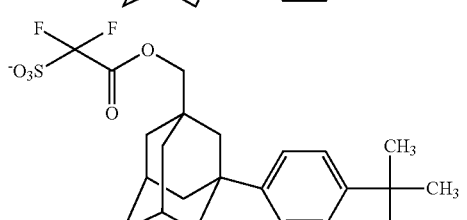
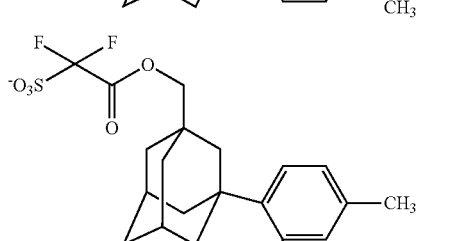
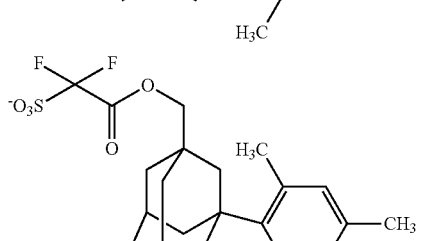
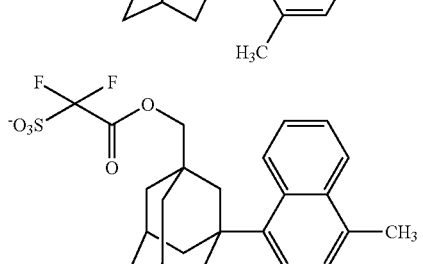
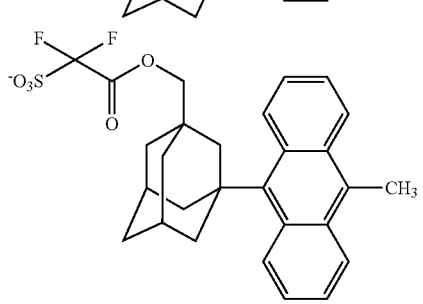

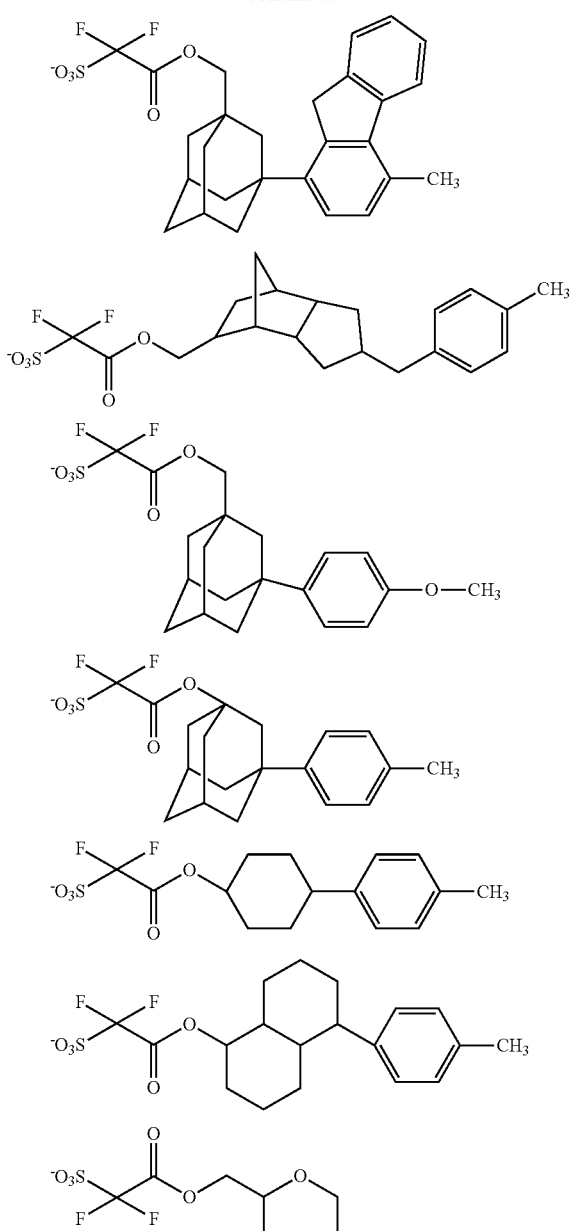
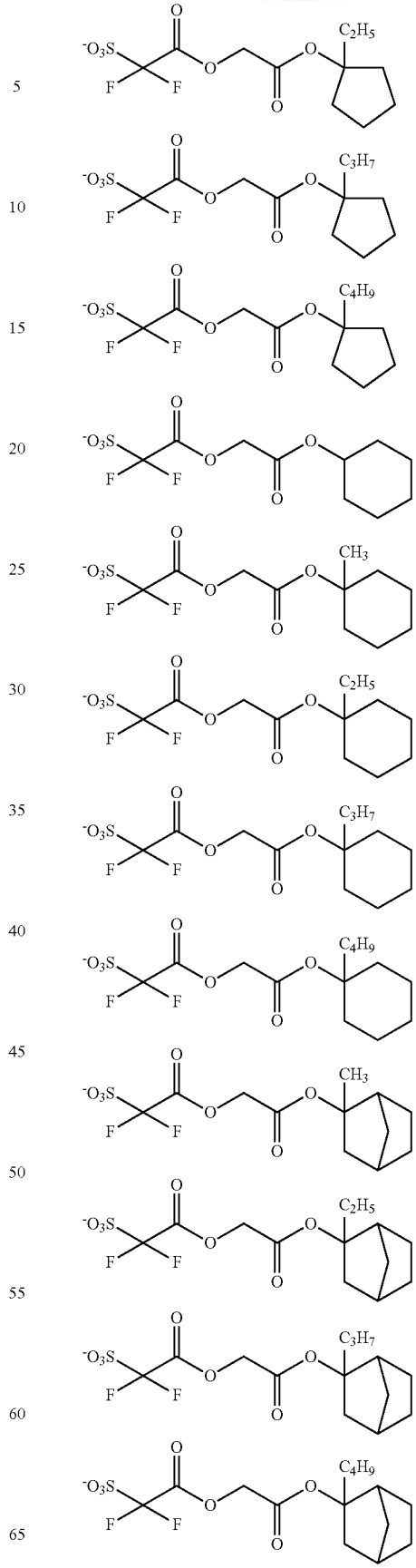
Examples of the anion part represented by the formula (c-b) include the followings.
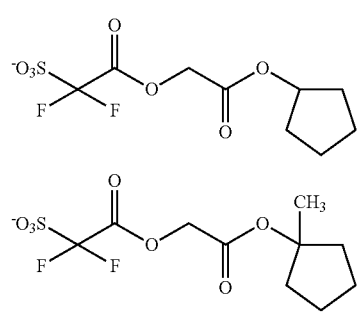

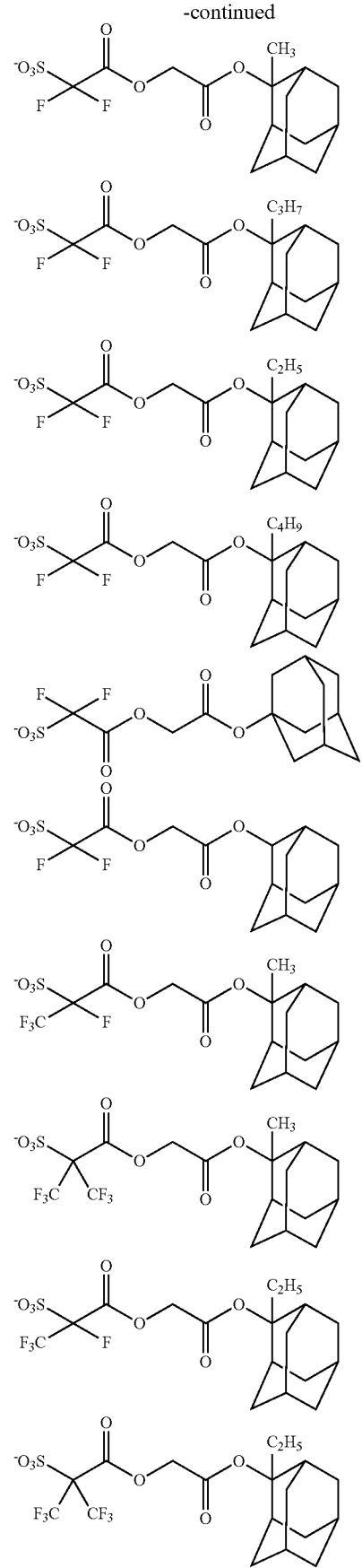
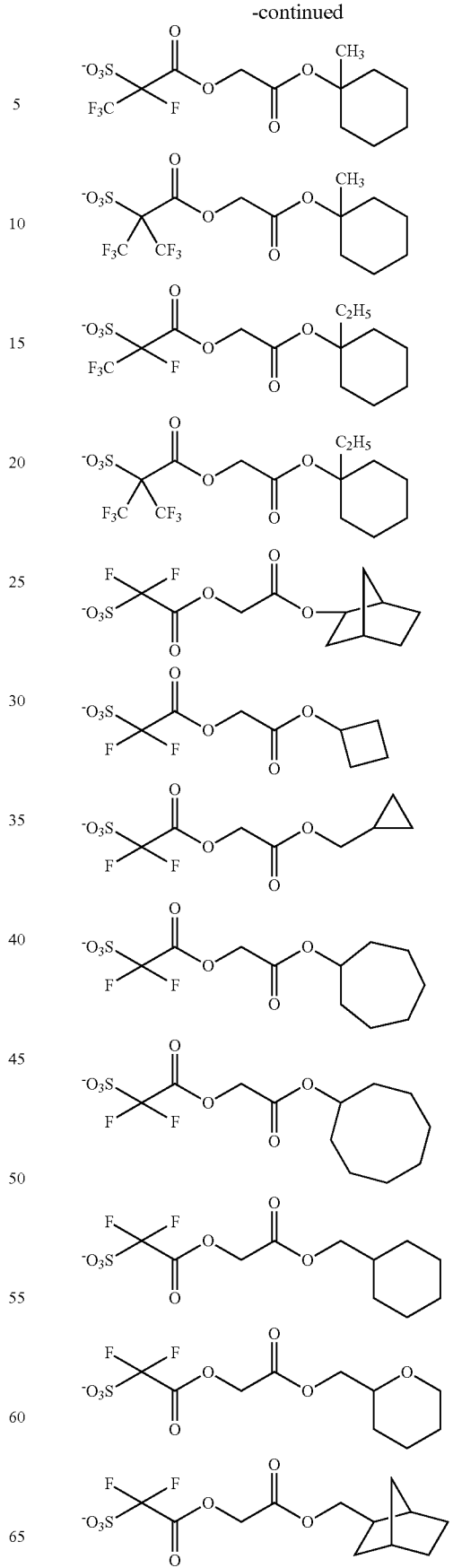

35
-continued
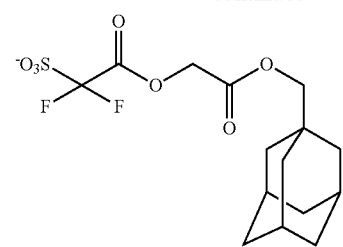
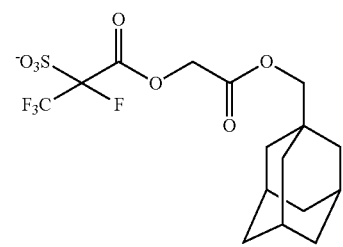
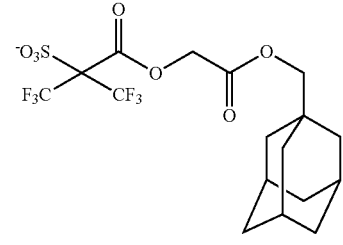
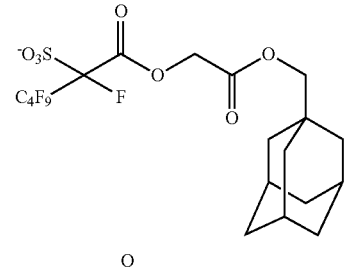
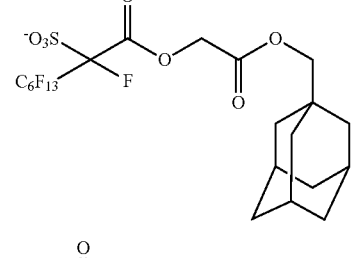
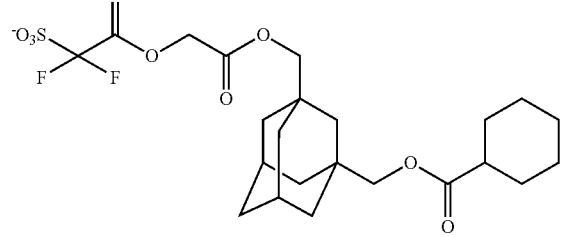
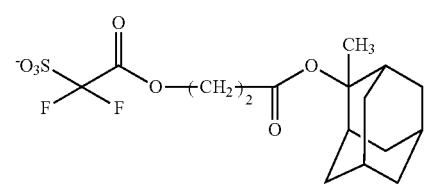
36
-continued
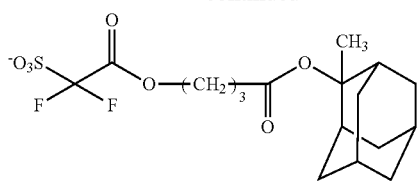
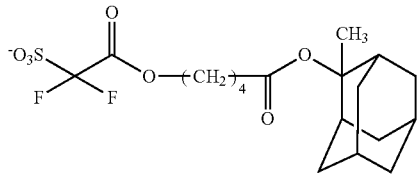
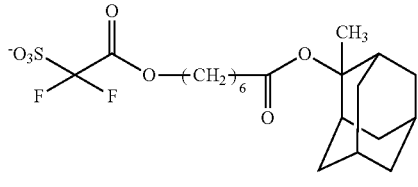
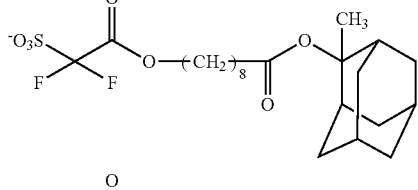
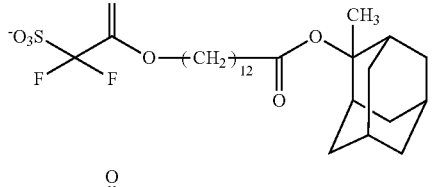
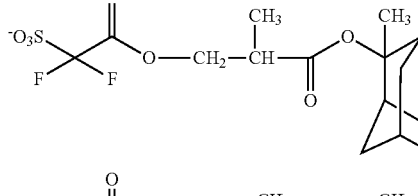
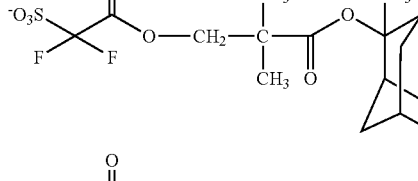
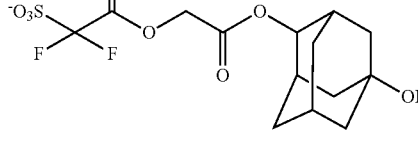
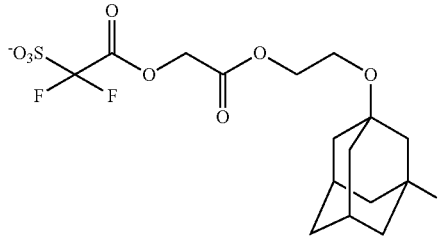

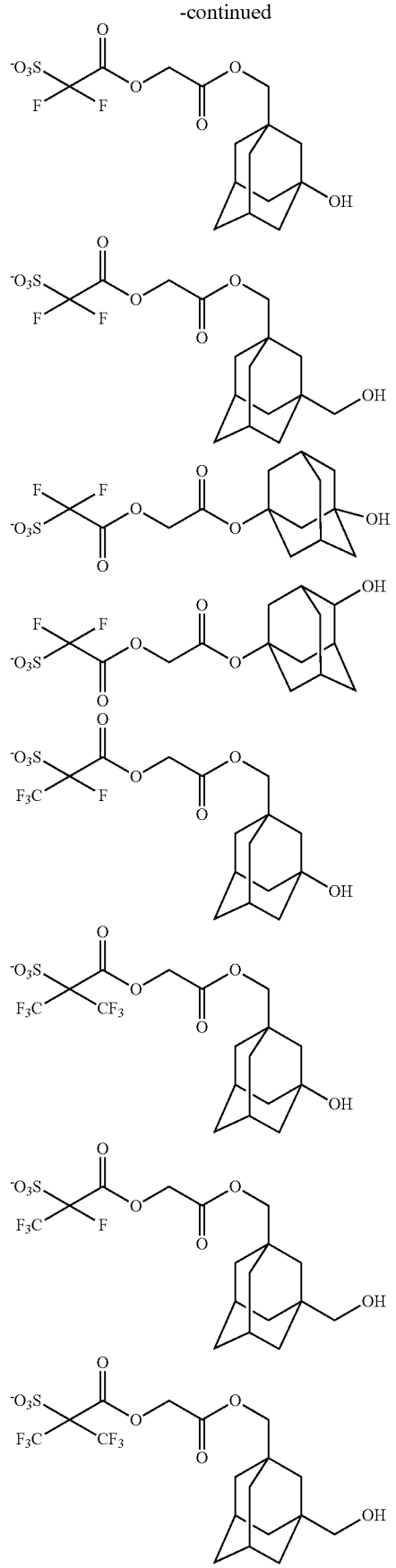
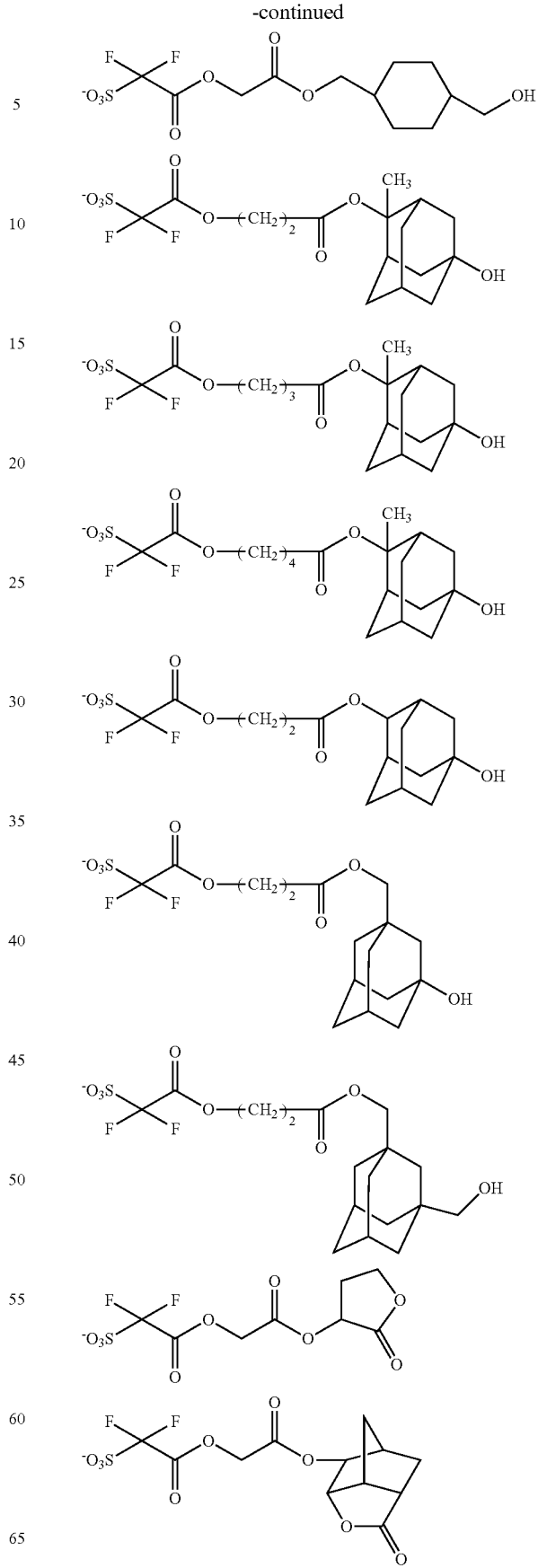

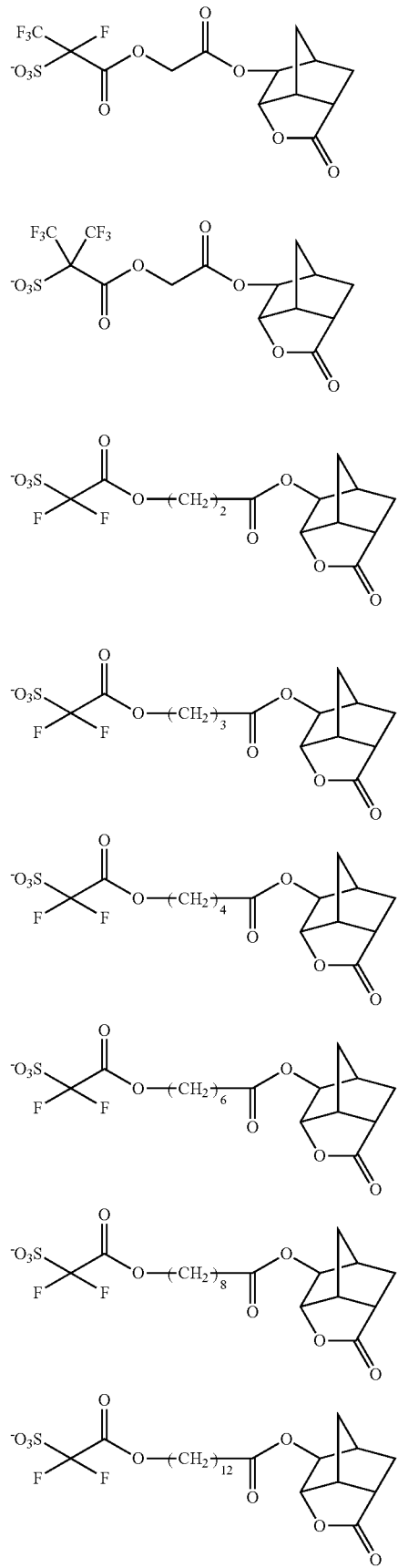
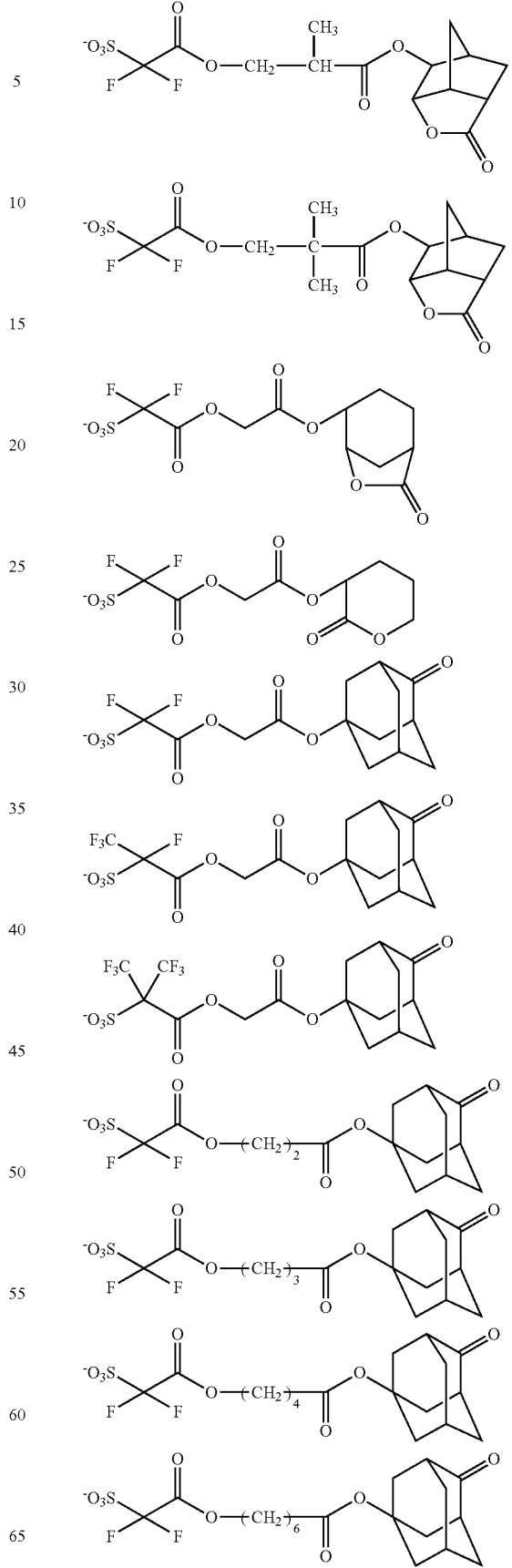

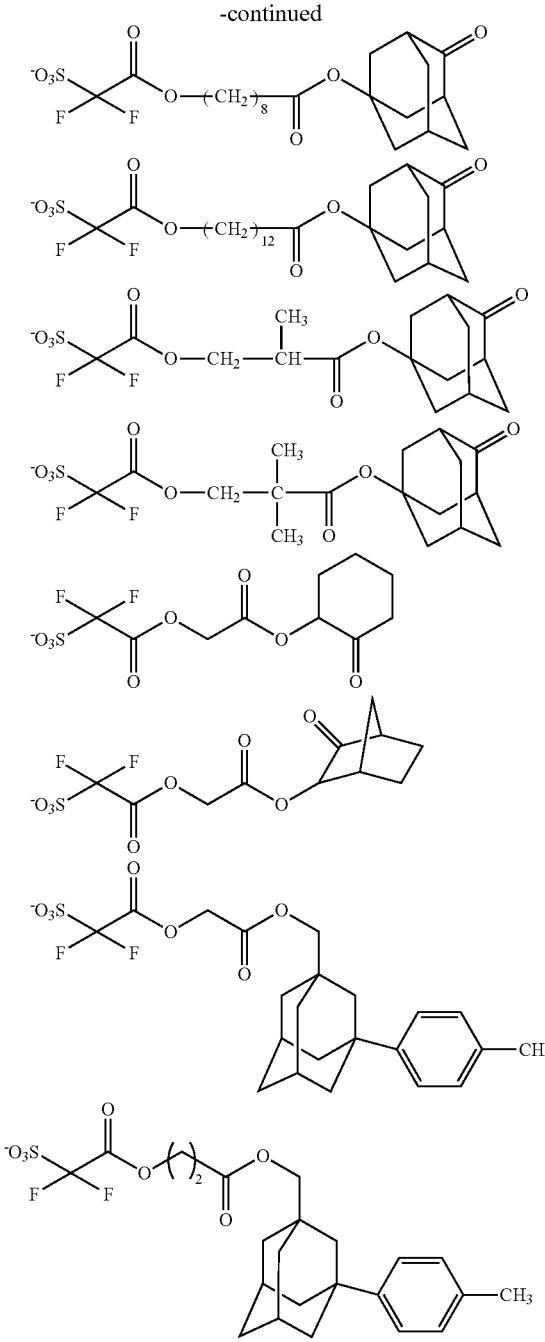
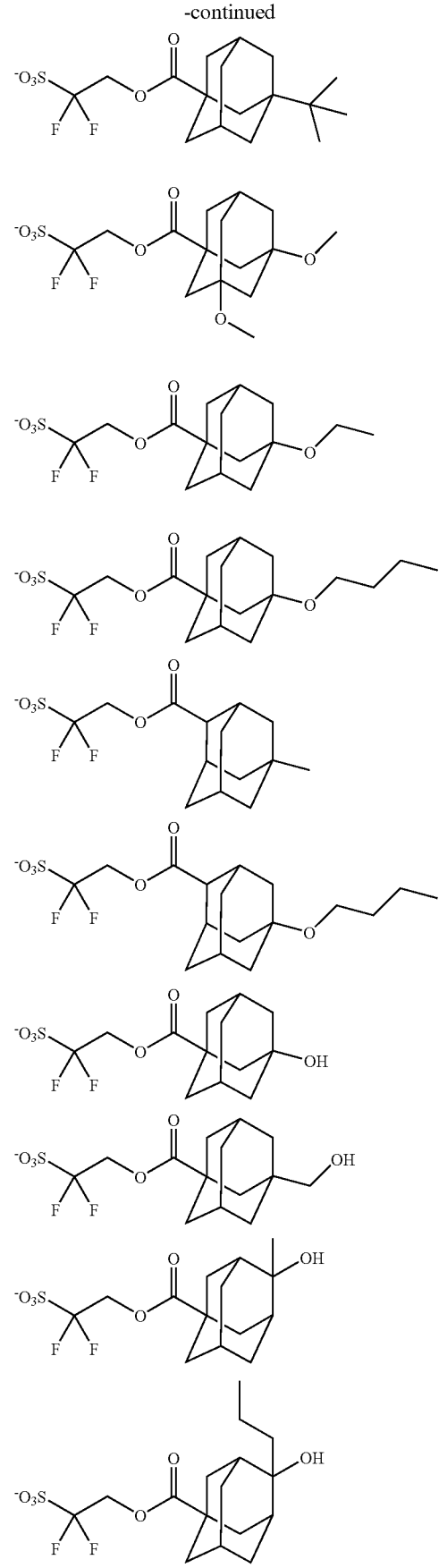
Examples of the anion part represented by the formula (c-c) include the followings.
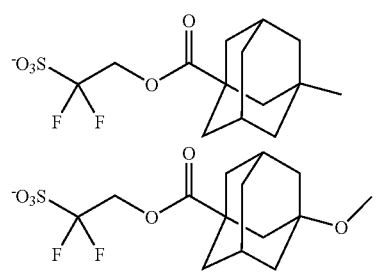

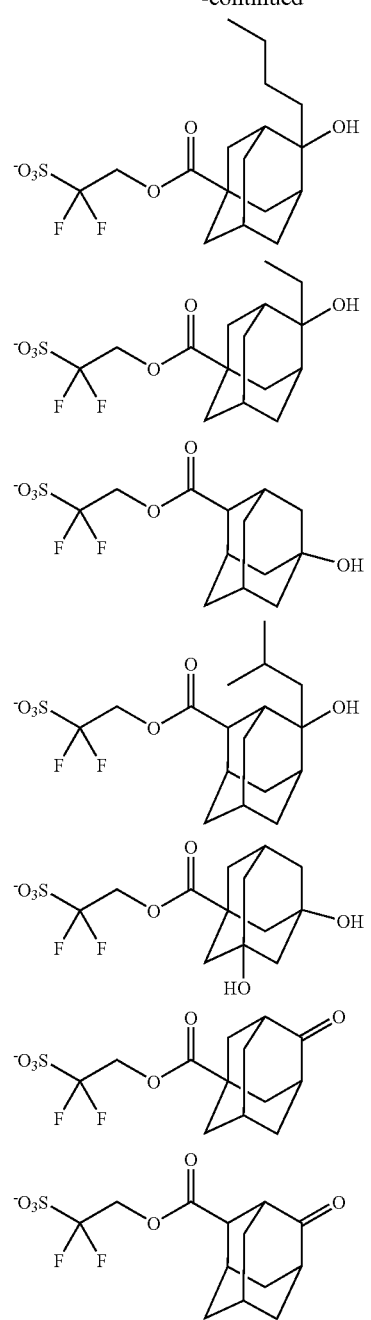
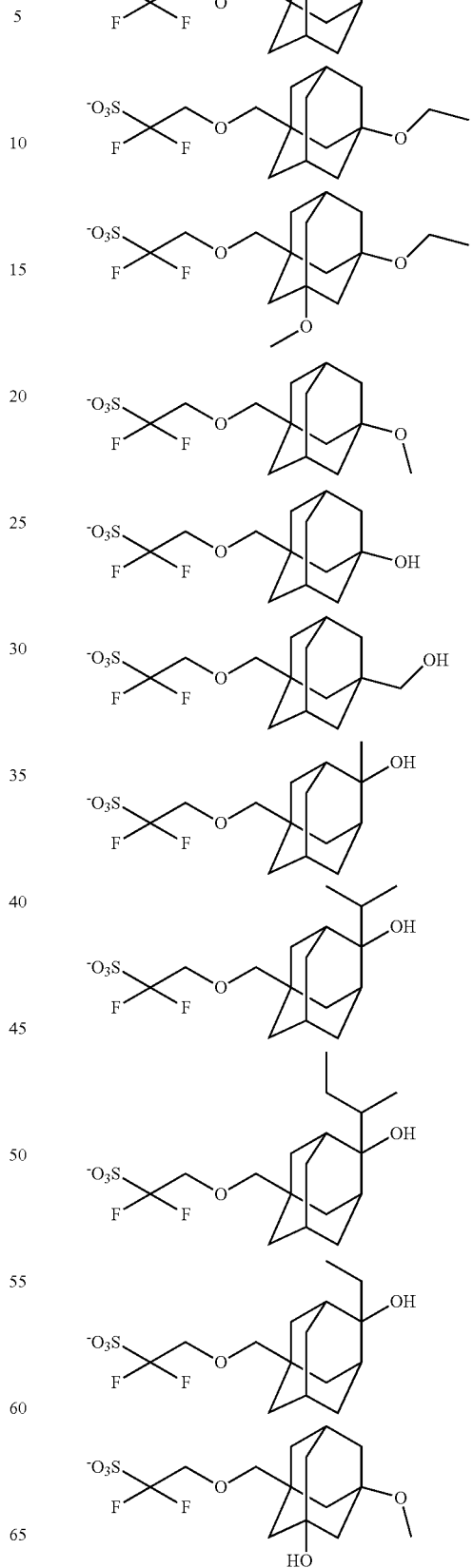
Examples of the anion part represented by the formula (c-d) include the followings.
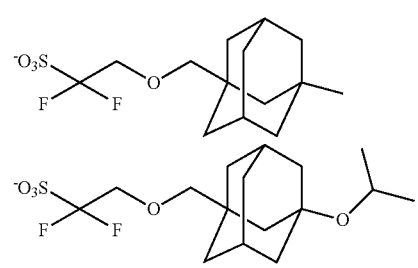

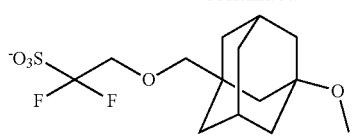
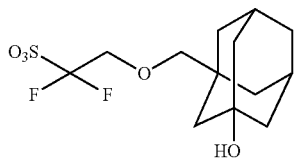
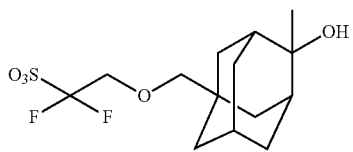
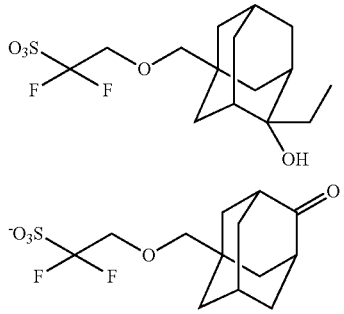
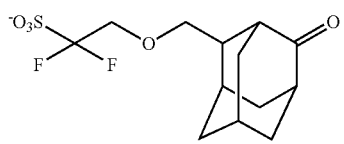

Examples of the anion part wherein $Y^1$ is the group represented by the formula (I) include the followings.

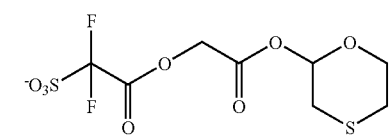
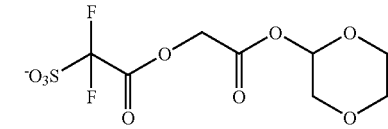
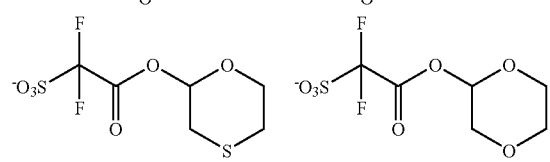

$Y^2$ in the cation part represented by the formula: $Y^2$—$Z^+$ of the salt represented by the formula (b1) represents a hydrogen atom or the group represented by the formula (I).

Examples of the cation part represented by the formula: $Y^2$—$Z^+$ wherein $Y^2$ is a hydrogen atom include the following cations represented by the formulae (IXa), (IXb), (IXc) and (IXd), and a cation represented by the formula (IXa) is preferable.

(IXa)

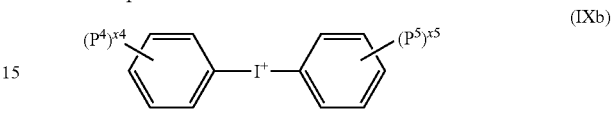

(IXb)

(IXc)

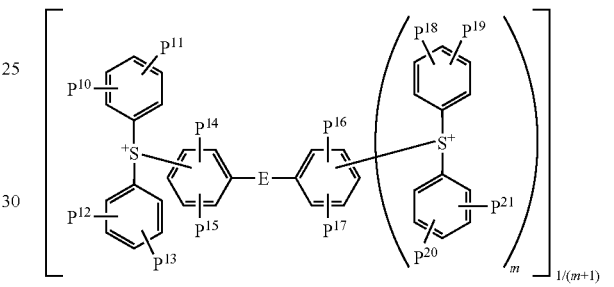

(IXd)

wherein $P^a$, $P^b$ and $P^c$ each independently represent a C1-C30 alkyl group which can have one or more substituents selected from the group consisting of a hydroxyl group, a C3-C12 alicyclic hydrocarbon group and a C1-C12 alkoxy group, a C3-C30 alicyclic hydrocarbon group which can have one or more substituents selected from the group consisting of a hydroxyl group, a C1-C12 alkyl group and a C1-C12 alkoxy group, or a C6-C20 aromatic hydrocarbon group which can have one or more substituents selected from the group consisting of a hydroxyl group, a C1-C12 alkyl group and a C1-C12 alkoxy group, and $P^a$ and $P^b$ can be bonded each other to form a ring, $P^4$ and $P^5$ are independently in each occurrence a hydrogen atom, a hydroxyl group, a C1-C12 alkyl group or a C1-C12 alkoxy group, x4 and x5 independently represents an integer of 1 to 5, and $P^6$ and $P^7$ each independently represent a C1-C12 alkyl group or a C3-C12 cycloalkyl group, or $P^6$ and $P^7$ are bonded to form a C3-C12 divalent acyclic hydrocarbon group which forms a ring together with the adjacent $S^+$, and one or more —$CH_2$— in the divalent acyclic hydrocarbon group may be replaced by —CO—, —O— or —S—, and $P^8$ represents a hydrogen atom, $P^9$ represents a C1-C12 alkyl group, a C3-C12 cycloalkyl group or a C6-C20 aromatic group which may be substituted, or $P^8$ and $P^9$ are bonded each other to form a divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $P^{10}$, $P^{11}$, $P^{12}$, $P^{13}$, $P^{14}$, $P^{15}$, $P^{16}$, $P^{17}$, $P^{18}$, $P^{19}$, $P^{20}$ and $P^{21}$ each independently represent a hydrogen atom, a hydroxyl group, a C1-C12 alkyl group or a C1-C12 alkoxy group, E represents a sulfur atom or an oxygen atom and m represents 0 or 1.

Examples of the alkyl group and the alicyclic hydrocarbon group include the same as described above.

Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the cycloalkyl group include a cyclohexyl group and an adamantyl group.

Examples of the C3-C12 divalent acyclic hydrocarbon group formed by bonding $P^6$ and $P^7$ include a trimethylene group, a tetramethylene group and a pentamethylene group. Examples of the ring group formed together with the adjacent $S^+$ and the divalent acyclic hydrocarbon group include a tetramethylenesulfonio group, a pentamethylenesulfonio group and an oxybisethylenesulfonio group.

Examples of the C6-C20 aromatic group include a phenyl group, a tolyl group, a xylyl group, a tert-butylphenyl group and a naphthyl group. Examples of the divalent acyclic hydrocarbon group formed by bonding $P^8$ and $P^9$ include a methylene group, an ethylene group, a trimethylene group, a tetramethylene group and a pentamethylene group and examples of the 2-oxocycloalkyl group formed together with the adjacent —CHCO— and the divalent acyclic hydrocarbon group include a 2-oxocyclopentyl group and a 2-oxocyclohexyl group.

The cation represented by the formula (IXa) wherein $P^a$, $P^b$ and $P^c$ each independently represent a C6-C20 aromatic hydrocarbon group which can have one or more substituents selected from the group consisting of a hydroxyl group, a C1-C12 alkyl group, and a C1-C12 alkoxy group, is preferable, and a cation represented by the formula (IXaa):

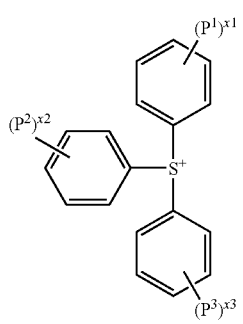

(IXaa)

wherein $P^1$, $P^2$ and $P^3$ are independently in each occurrence a hydrogen atom, a hydroxyl group, a C1-C12 alkyl group or a C1-C12 alkoxy group, and x1, x2 and x3 independently represents an integer of 1 to 5, is more preferable.

Examples of the alicyclic hydrocarbon group include a group having an adamantane structure or an isobornane structure, and a 2-alkyl-2-adamantyl group, a 1-(1-adamantyl)-1-alkyl group and an isobornyl group are preferable.

Examples of the cation represented by the formula (IXaa) include the followings.

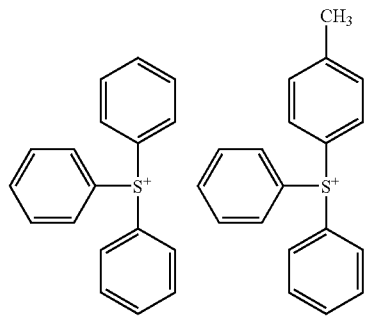

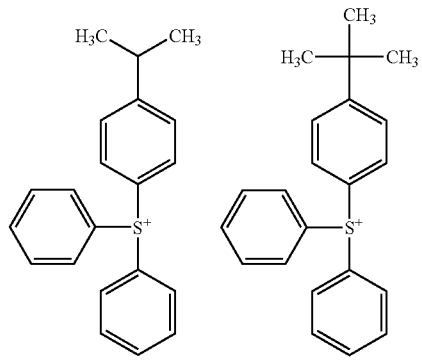

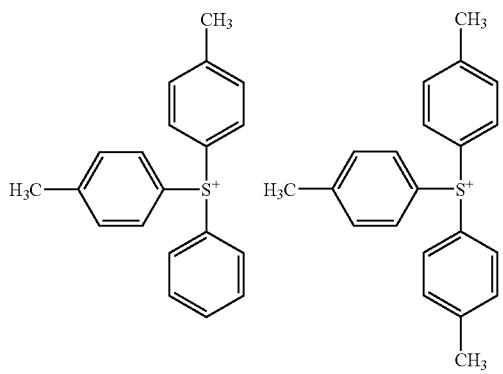

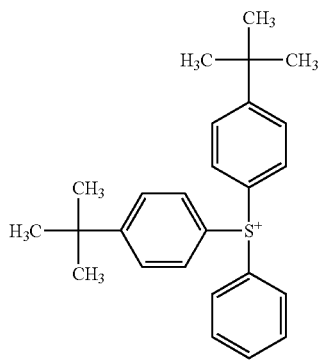

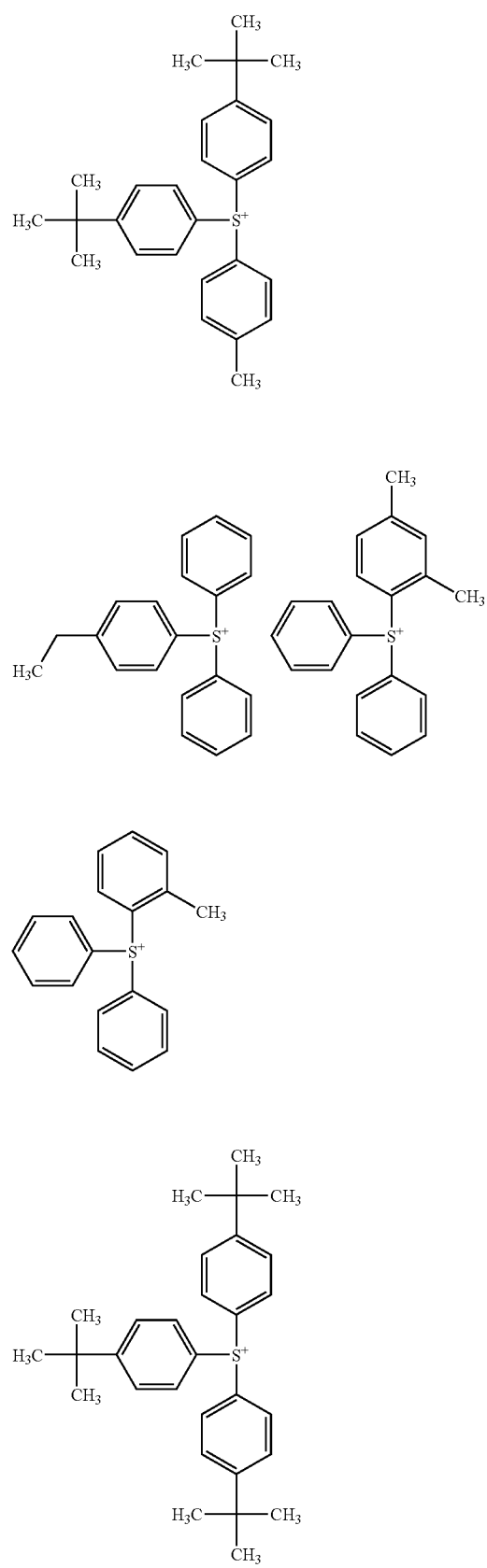

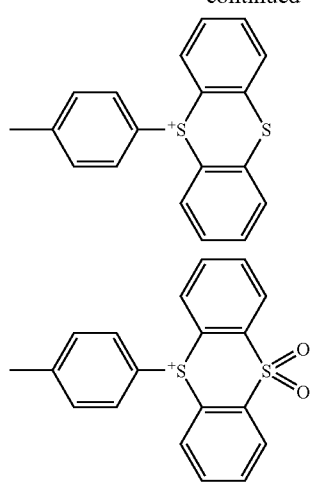
Examples of the cation represented by the formula (IXb) include the followings.
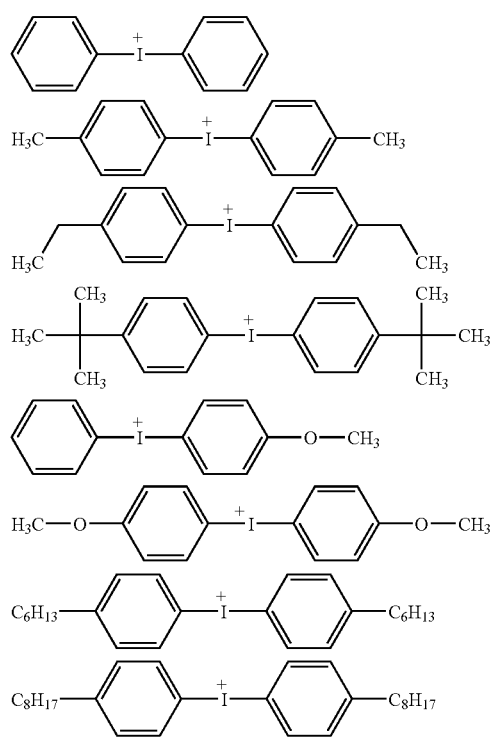
Examples of the cation represented by the formula (IXc) include the followings.
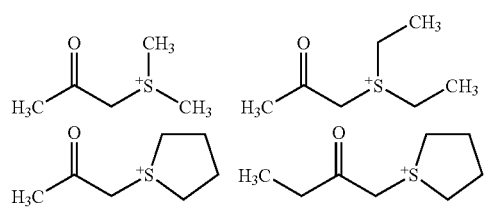
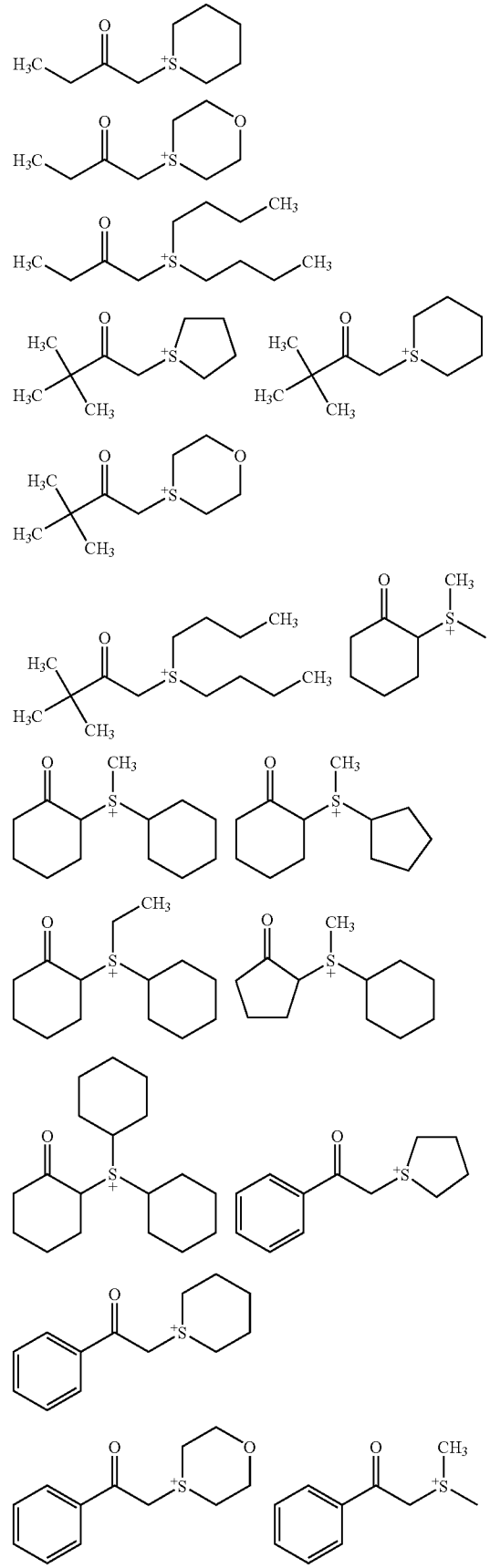

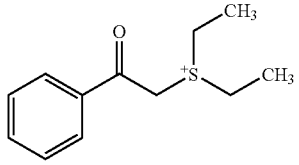
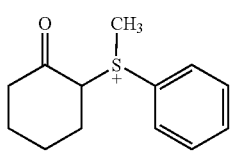
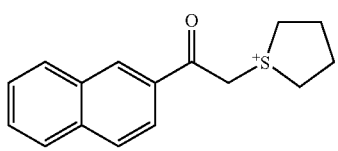
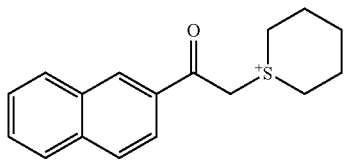
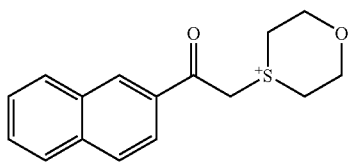
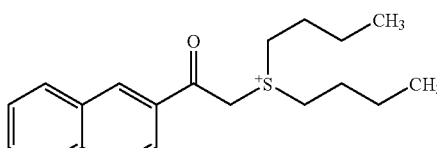
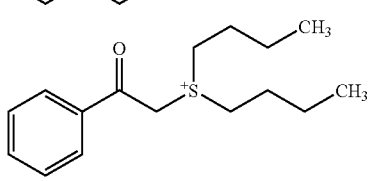
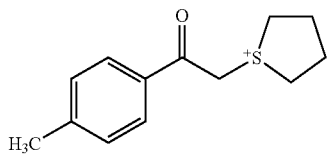
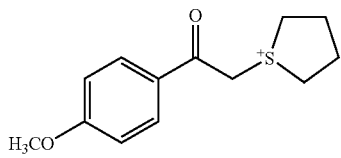
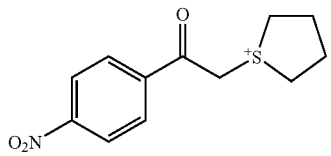
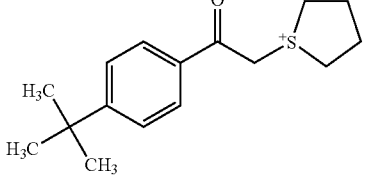
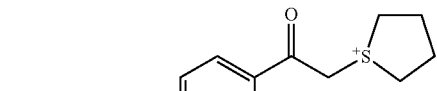
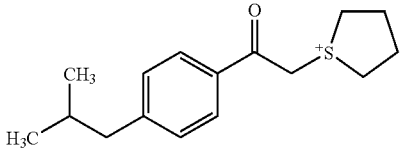
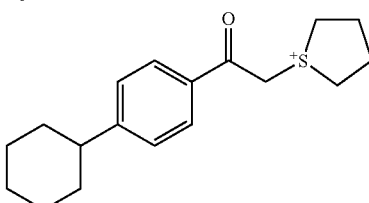
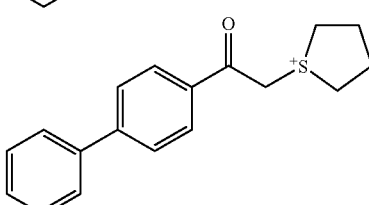
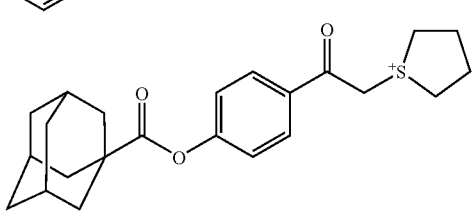
Examples of the cation represented by the formula (IXd) include the followings.
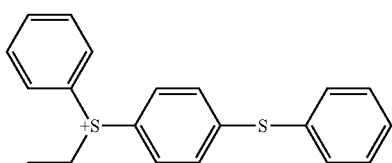
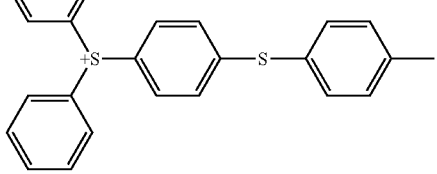

55
-continued
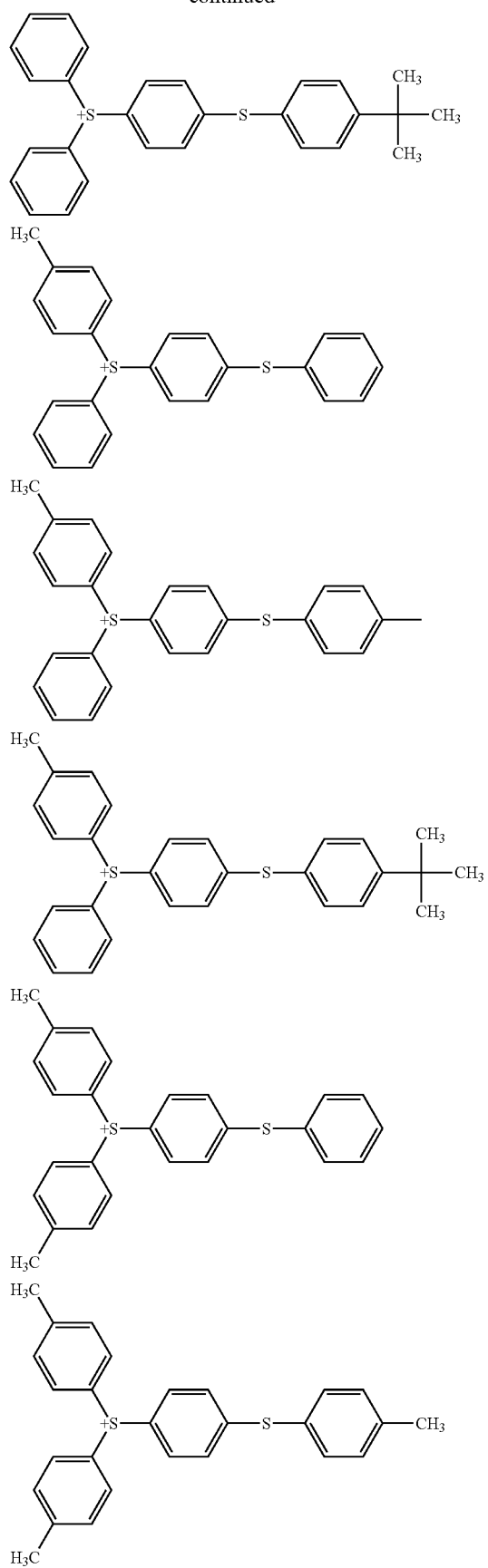
56
-continued
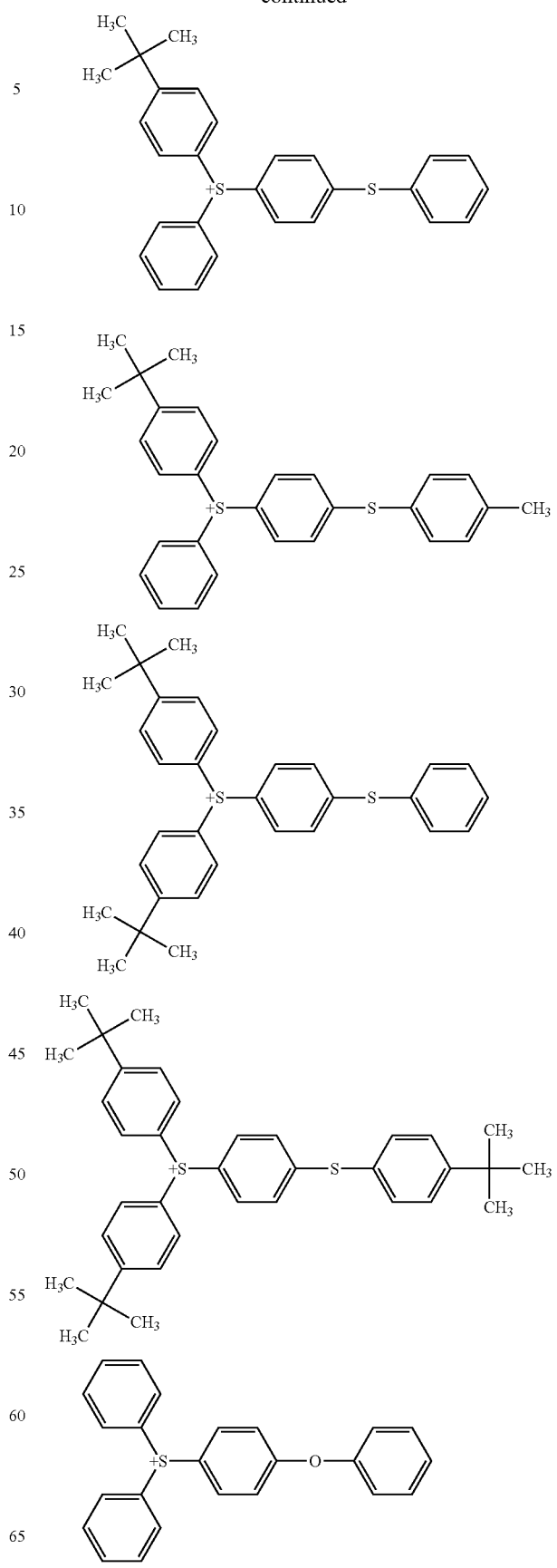

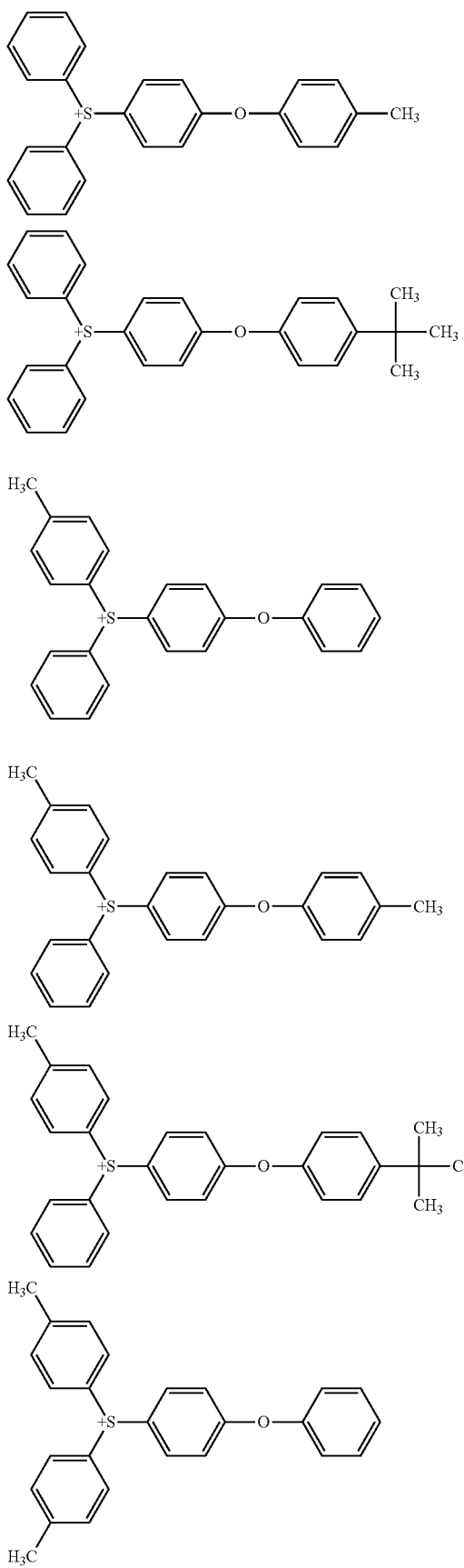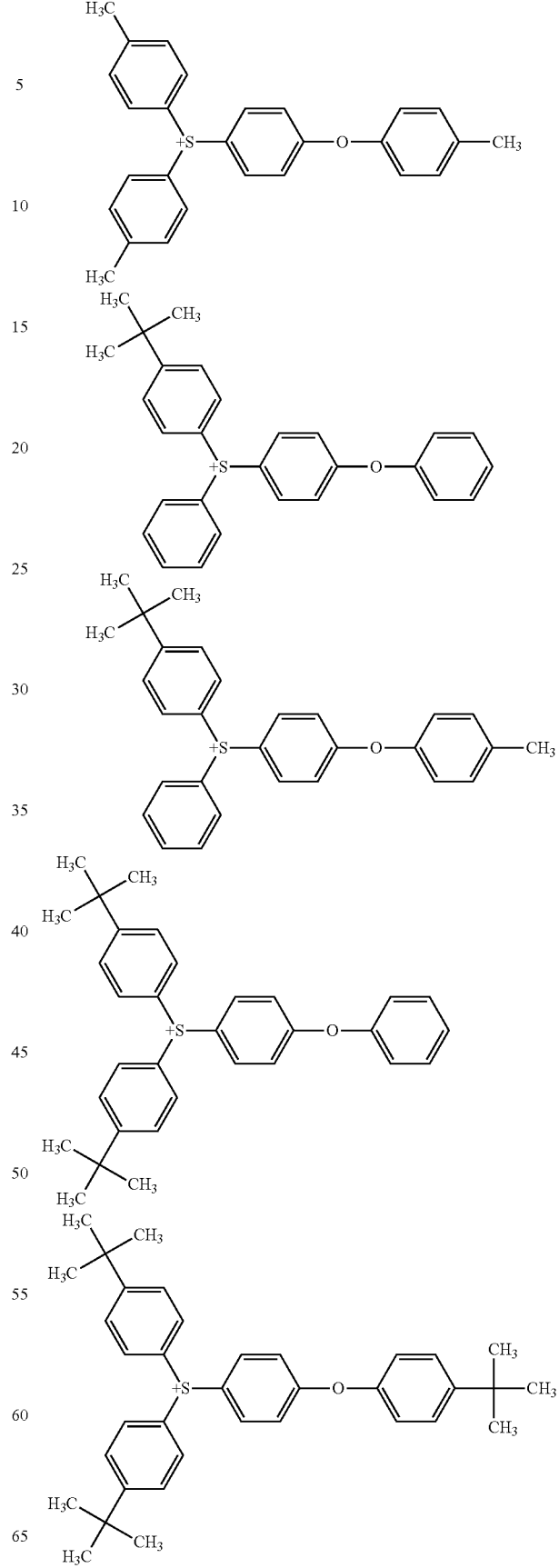

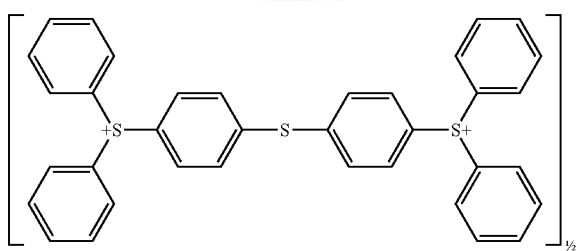
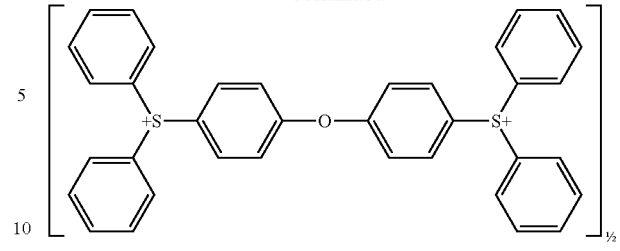
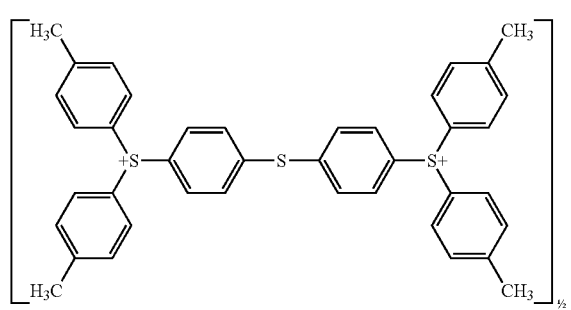
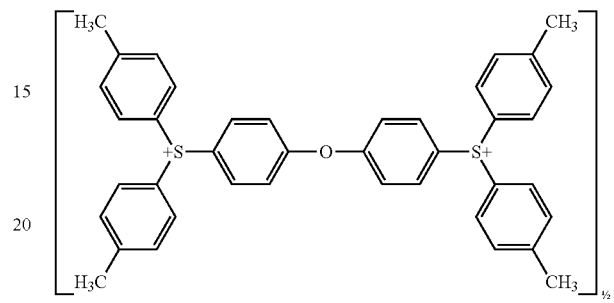
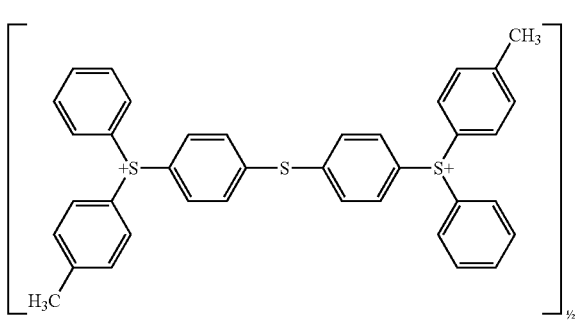
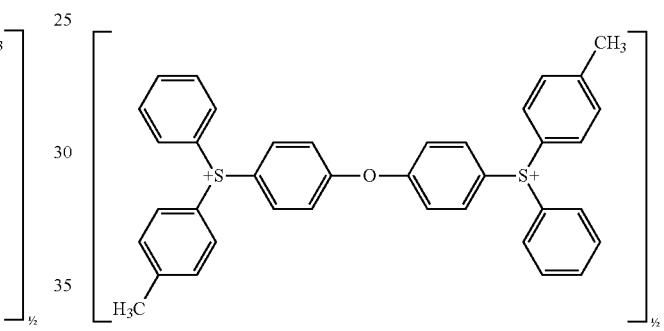
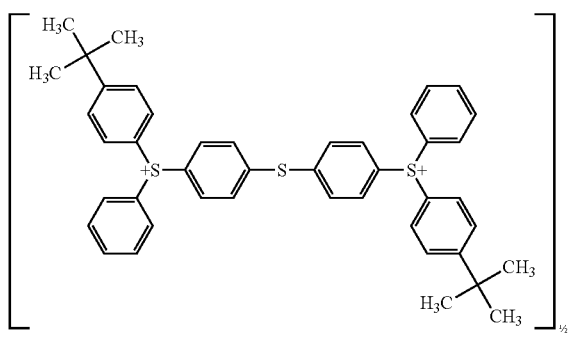
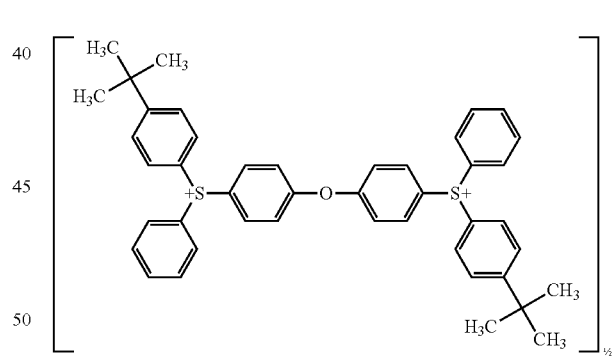
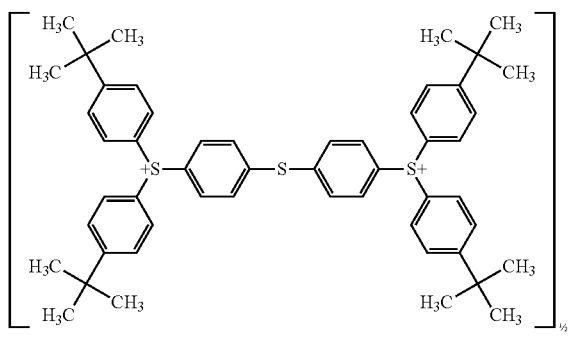
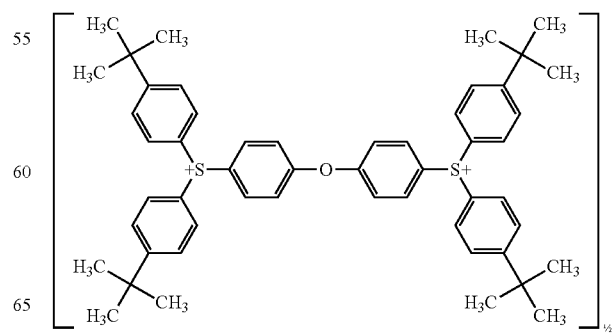

Among them, a triarylsulfonium ion is preferable.

Examples of the group containing the group represented by the formula (I) include a group represented by the formula (I-3):

$$-A-T \quad (I-3)$$

wherein T is the same as defined above, and A represents a C1-C17 saturated hydrocarbon group which can have one or more substituents, and one or more methylene groups in the saturated hydrocarbon group can be replaced by —O— or —CO—.

Examples of the C1-C17 saturated hydrocarbon group include the same as described in $X^1$, and groups represented by the formulae (A-1), (A-2) and (A-3) are preferable.

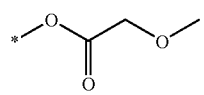

(A-1)

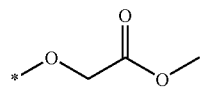

(A-2)

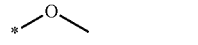

(A-3)

wherein * represents a binding position to T.

Examples of the cation part represented by the formula: $Y^2$—$Z^+$ wherein $Y^2$ is a group containing the group represented by the formula (I) include those wherein a hydrogen atom in the above-mentioned cations represented by the formula: $Y^2$—$Z^+$ wherein $Y^2$ is a hydrogen atom is replaced by the group containing the group represented by the formula (I). Among them, a cation represented by the formula (VIII) is preferable.

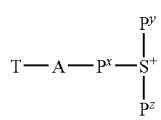

(VIII)

wherein $P^x$ represents a C1-C30 alkylene group which can have one or more substituents, a C3-C30 divalent alicyclic hydrocarbon group which can have one or more substituents, or a C6-C20 divalent aromatic hydrocarbon group which can have one or more substituents, $P^y$ and $P^z$ independently each represent a C1-C30 alkyl group which can have one or more substituents, a C3-C30 alicyclic hydrocarbon group which can have one or more substituents or a C6-C20 aromatic hydrocarbon group which can have one or more substituents, or $P^y$ and $P^z$ are bonded each other to form a ring, and A and T are the same as defined above.

The cation represented by the formula (VIII) wherein $P^x$ is a C6-C20 divalent aromatic hydrocarbon group which can have one or more substituents, and $P^y$ and $P^z$ independently each represent a C6-C20 aromatic hydrocarbon group which can have one or more substituents is preferable.

Examples of the cation represented by the formula (VIII) include the followings:

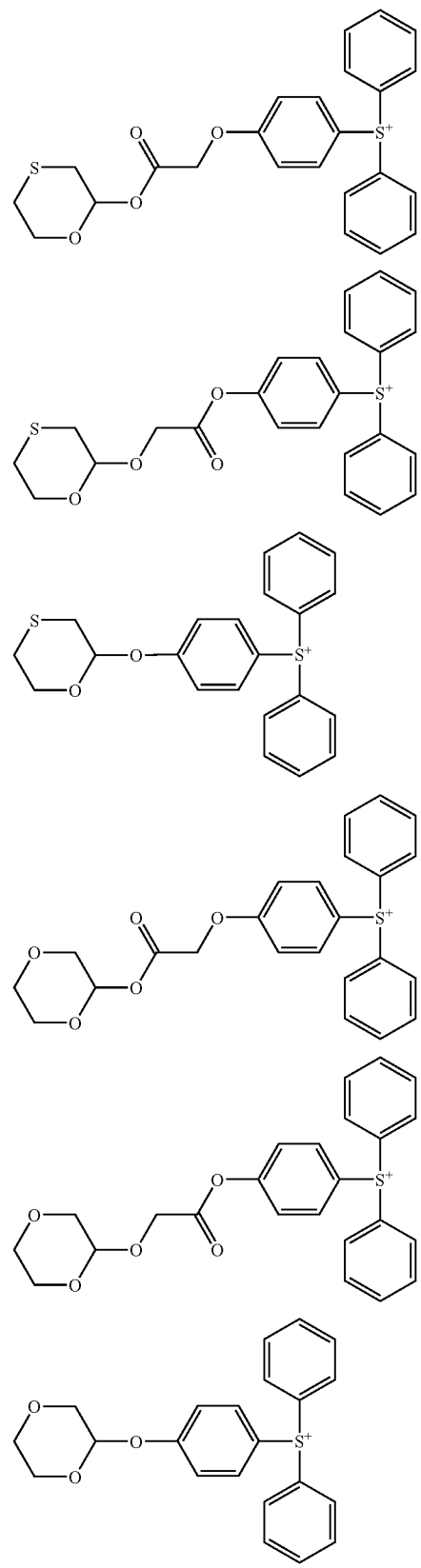

Examples of the salt having a group containing the group represented by the formula (I) include the followings.

63 64
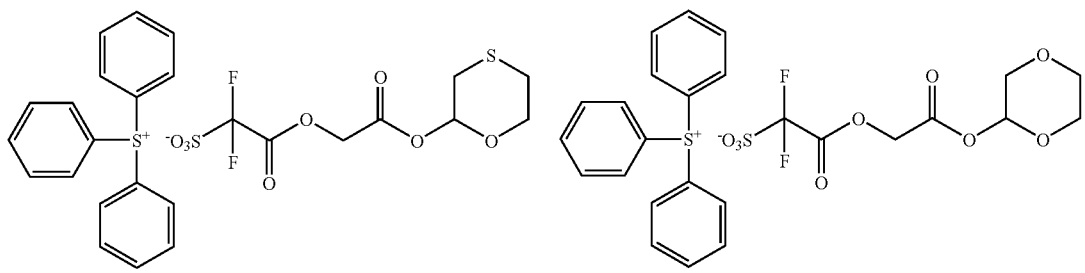
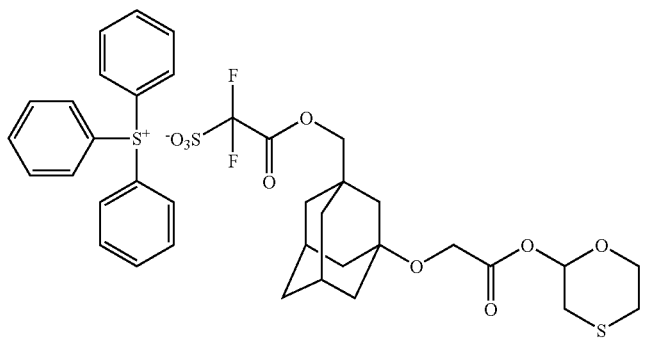
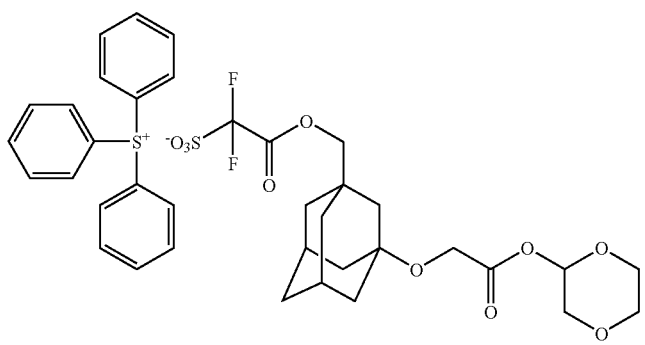
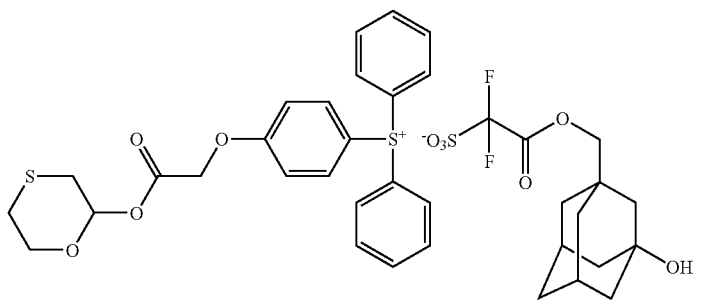
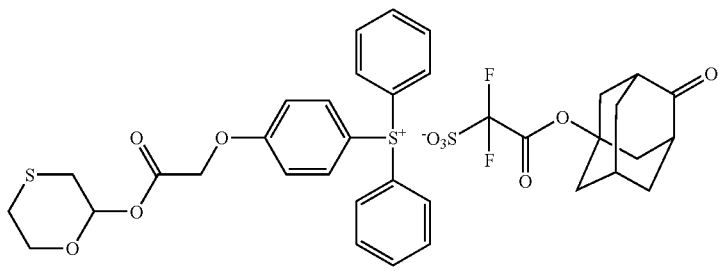

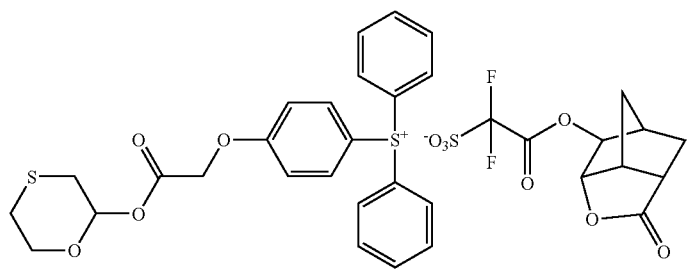
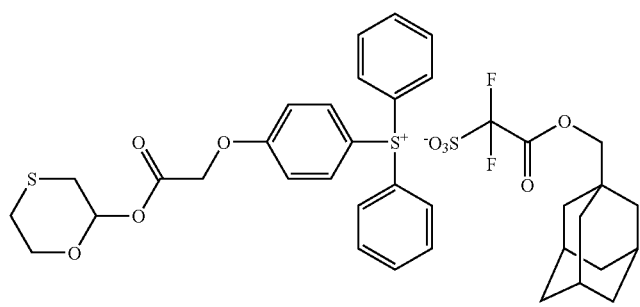
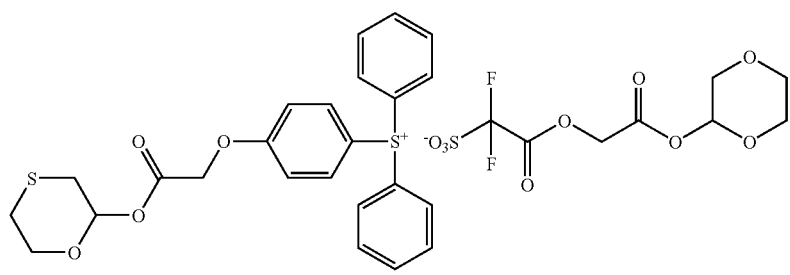
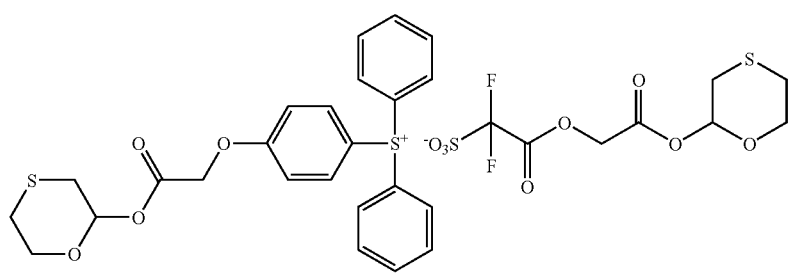
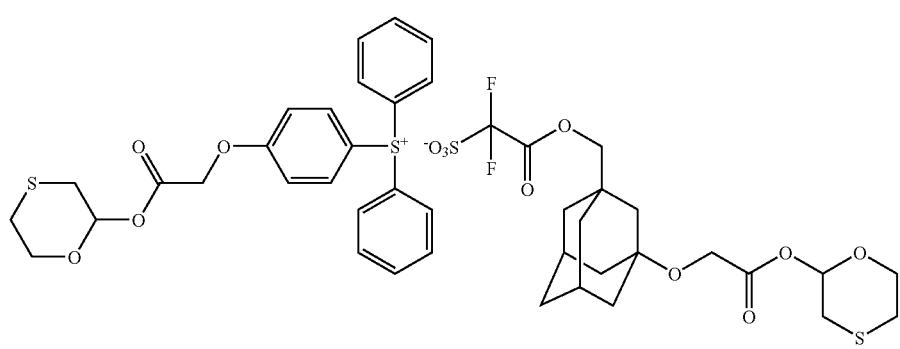

-continued

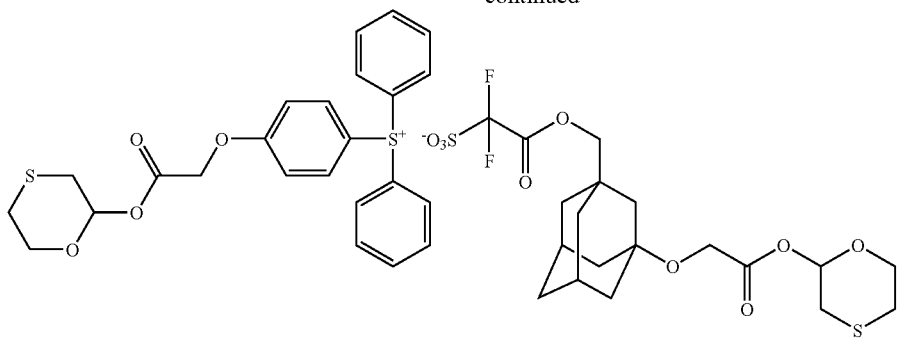

The salt having a group represented by the formula (I) can be produced according to known methods in the art.

For example, a salt represented by the formula (Ia), which has the group represented by the formula (I), can be produced by reacting a salt represented by the formula (Ia-1) with a compound represented by the formula (Ia-2) in a solvent in the presence of a catalyst.

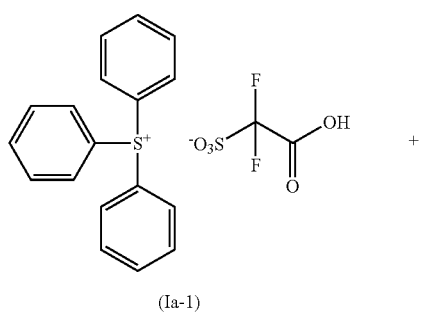

(Ia-1)

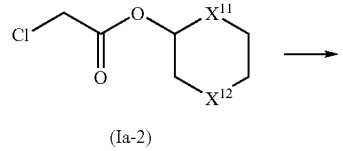

(Ia-2)

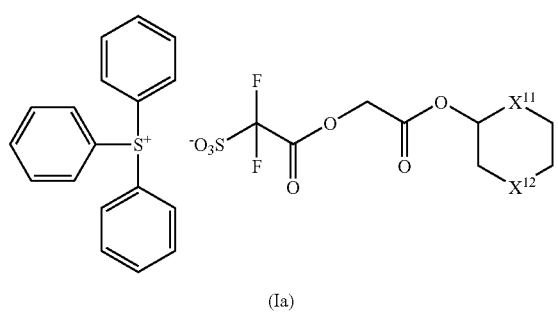

(Ia)

The salt represented by the formula (Ia-1) can be produced according to the method described in JP 2008-13551 A.

The compound represented by the formula (Ia-2) can be produced by reacting a compound represented by the formula (Ia-3) with a compound represented by the formula (Ia-4) in a solvent such as tetrahydrofuran in the presence of a catalyst such as pyridine.

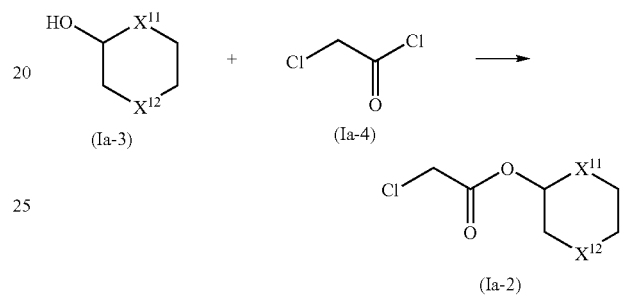

The compound represented by the formula (Ia-3) can be produced by hydrolyzing a compound represented by the formula (Ia-5) in a solvent such as dimethylsulfoxide in the presence of a catalyst such as hydrochloric acid.

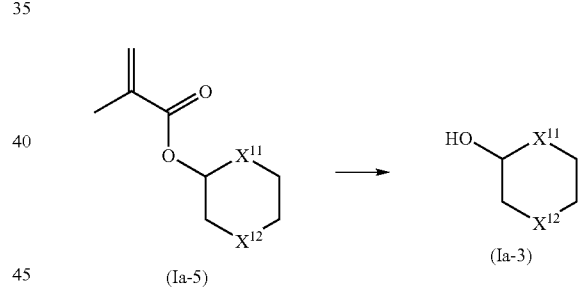

Examples of the compound represented by the formula (Ia-5) include the following compound:

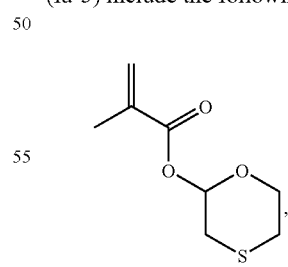

which is available from KURARAY, CO., LTD.

For example, a salt represented by the formula (Ib), which has the group represented by the formula (I), can be produced by reacting a salt represented by the formula (Ib-1) with a salt represented by the formula (Ib-2) in a solvent such as chloroform.

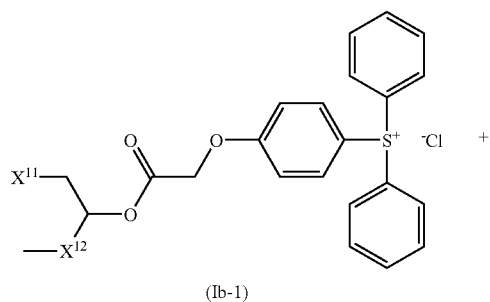

(Ib-1)

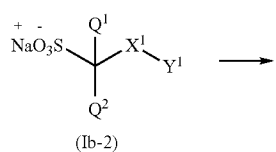

(Ib-2)

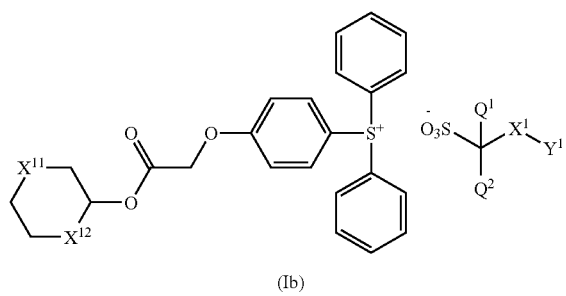

(Ib)

The salt represented by the formula (Ib-2) can be produced according to the method described in JP 2008-165218 A.

The salt represented by the formula (Ib-1) can be produced by reacting a salt represented by the formula (Ib-3) with the compound represented by the formula (Ia-2) in a solvent such as N,N-dimethylformamide in the presence of a catalyst such as potassium carbonate and potassium iodide.

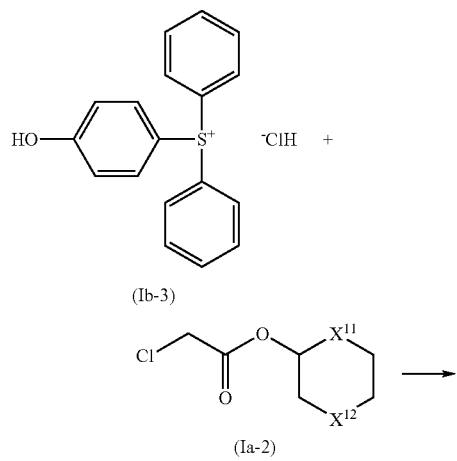

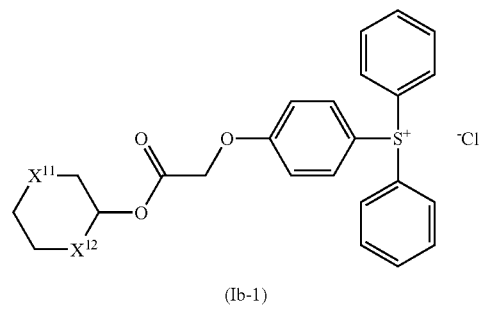

(Ib-1)

The photoresist composition of the present invention comprises a salt having a group containing a group represented by the formula (I) and a resin comprising a structural unit having an acid-labile group and being insoluble or poorly soluble in an aqueous alkali solution but becoming soluble in an aqueous alkali solution by the action of an acid.

The photoresist composition can contain two or more kinds of the salt having a group containing a group represented by the formula (I). The photoresist composition can contain two or more kinds of the resins.

The salt having a group containing a group represented by the formula (I) works as an acid generator in the photoresist composition. The photoresist composition also can contain one or more acid generators other than the salt having a group containing a group represented by the formula (I).

Examples of the acid generators other than the salt having a group containing a group represented by the formula (I) include the followings.

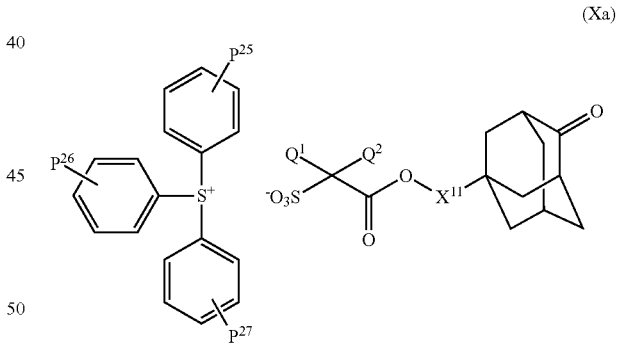

(Xa)

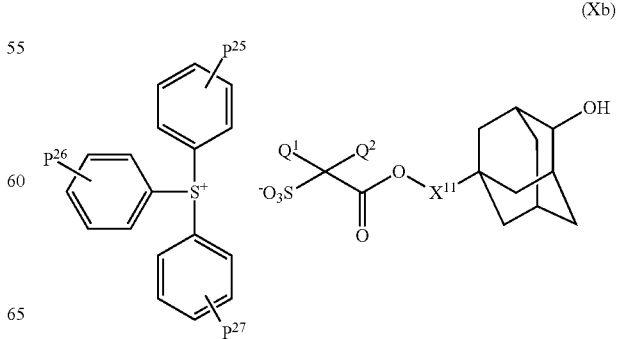

(Xb)

(Xc)
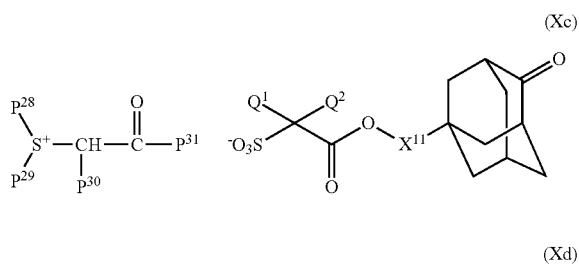

(Xd)
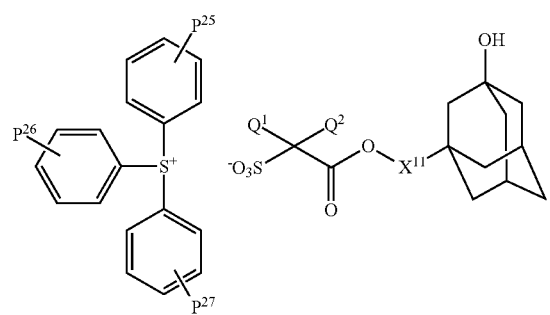

(Xe)
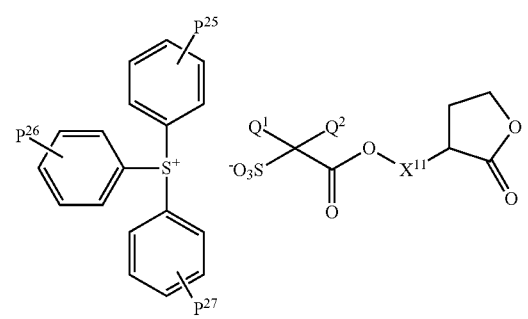

(Xf)
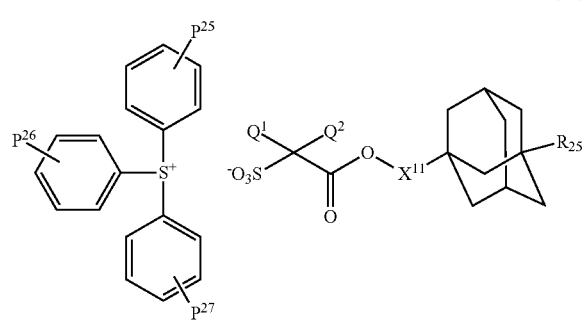

(Xg)
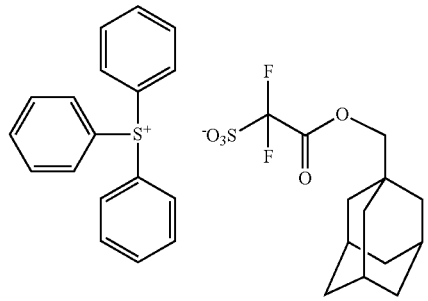

(Xh)
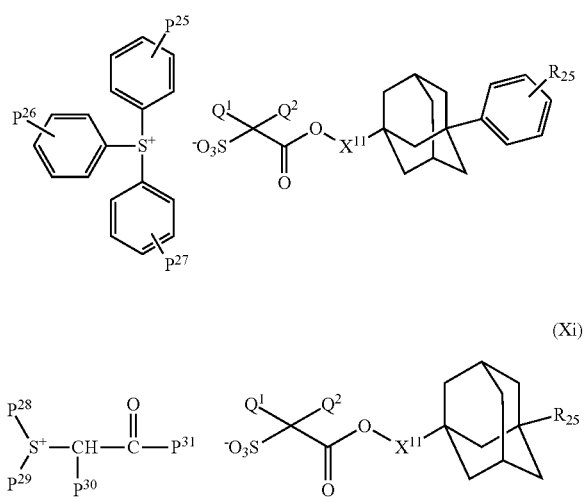

(Xi)

wherein $Q^1$ and $Q^2$ are the same as defined above, $P^{25}$, $P^{26}$ and $P^{27}$ independently each represent a hydrogen atom, a C1-C4 aliphatic hydrocarbon group or a C4-C36 alicyclic hydrocarbon group, $P^{28}$ and $P^{29}$ independently each represent a C1-C12 aliphatic hydrocarbon group or a C4-C36 alicyclic hydrocarbon group, or $P^{28}$ and $P^{29}$ are bonded each other to form a C2-C6 ring containing $S^+$, $P^{30}$ represents a C1-C12 aliphatic hydrocarbon group, a C4-C36 alicyclic hydrocarbon group or a C6-C20 aromatic group which may be substituted, or $P^{30}$ and $P^{31}$ are bonded each other to form a C3-C12 ring containing —CHCO—, and one or more —$CH_2$— in the ring can be replaced by —CO—, —O— or —S—, and $X^{11}$ represents a single bond or a methylene group, and $R^{25}$ represents a hydrogen atom, a hydroxyl group or a methyl group.

Examples of the ring formed by bonding $P^{28}$ and $P^{29}$ include a tetrahydrothiophenium group. Examples of the ring formed by bonding $P^{30}$ and $P^{31}$ include the above-mentioned groups represented by the formulae (W13) to (W15).

Preferable examples of the acid generators other than the salt having a group containing a group represented by the formula (I) include the followings.

-continued
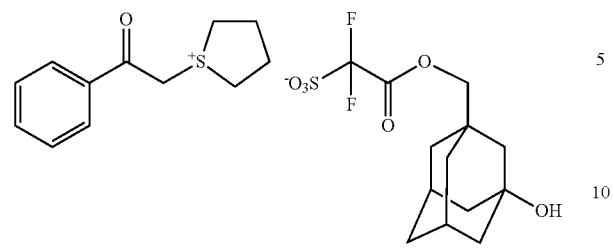
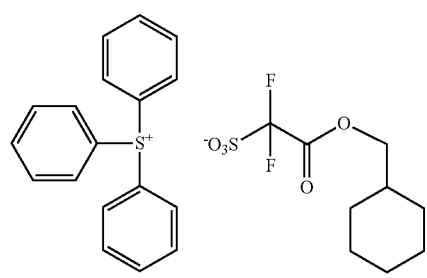
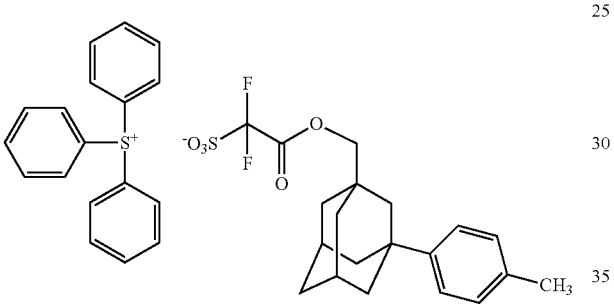
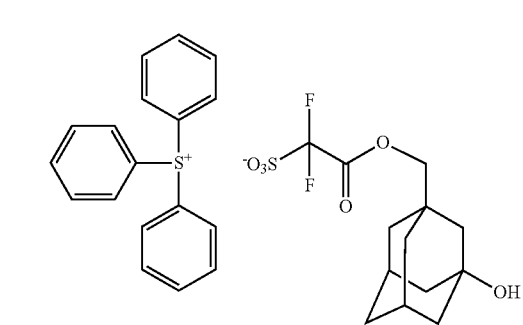
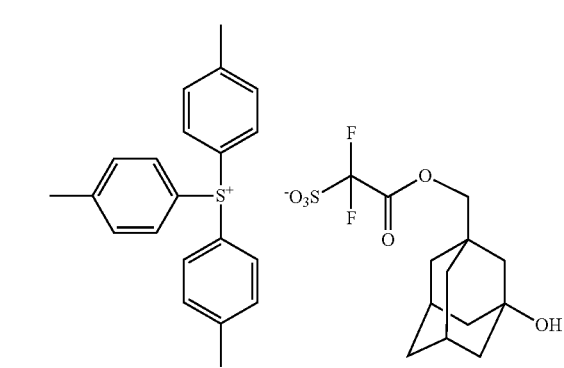
-continued
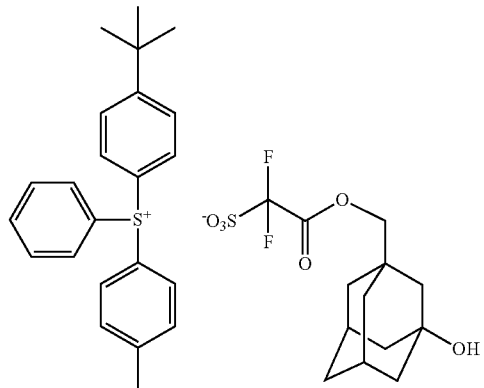
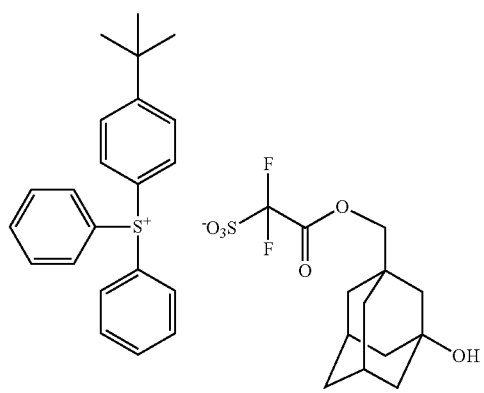
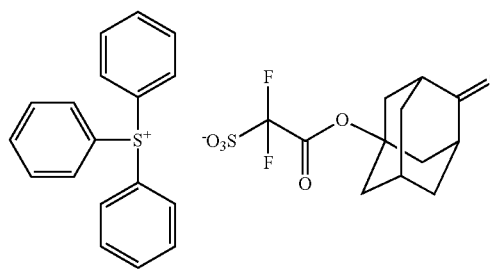
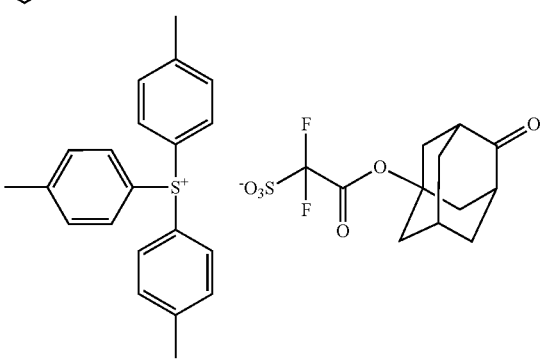

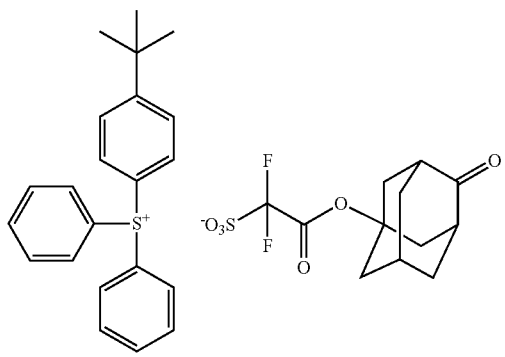

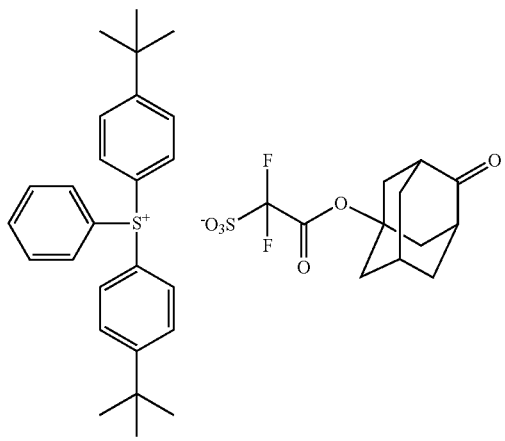

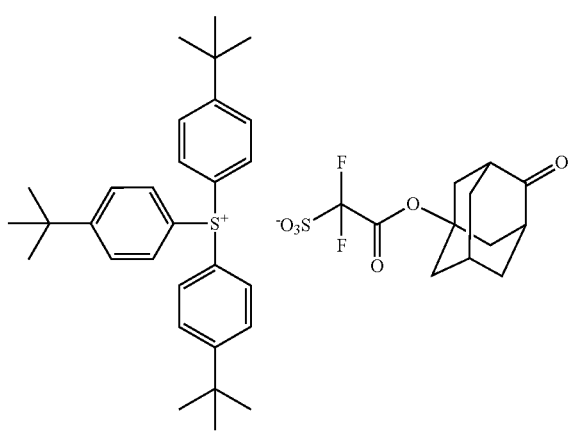

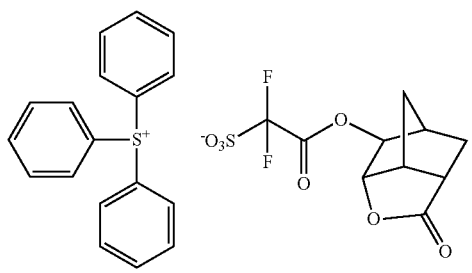

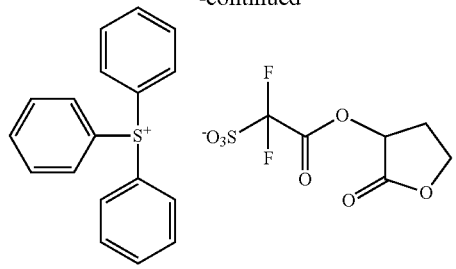

In this specification, "an acid-labile group" means a group capable of being eliminated by the action of an acid.

Examples of the acid-labile group include a group represented by the formula (10):

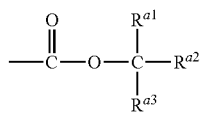 (10)

wherein $R^{a1}$, $R^{a2}$ and $R^{a3}$ independently each represent a C1-C8 aliphatic hydrocarbon group or a C3-C20 alicyclic hydrocarbon group, or $R^{a1}$ and $R^{a2}$ are bonded each other to form a C3-C20 ring.

Examples of the C1-C8 aliphatic hydrocarbon group include a C1-C8 alkyl group such as a methyl group, an ethyl group, a propyl group, an isopropyl group, a butyl group, a pentyl group, a hexyl group, a heptyl group and an octyl group. The C3-C20 alicyclic hydrocarbon group may be monocyclic or polycyclic, and examples thereof include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

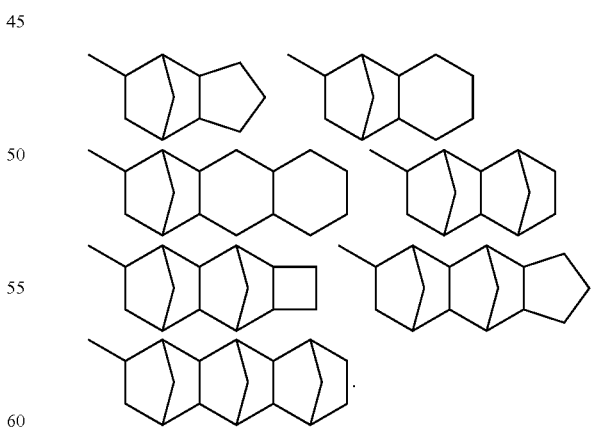

The alicyclic hydrocarbon group preferably has 3 to 16 carbon atoms.

Examples of the ring formed by bonding $R^{a1}$ and $R^{a2}$ each other include the following groups and the ring preferably has 3 to 12 carbon atoms.

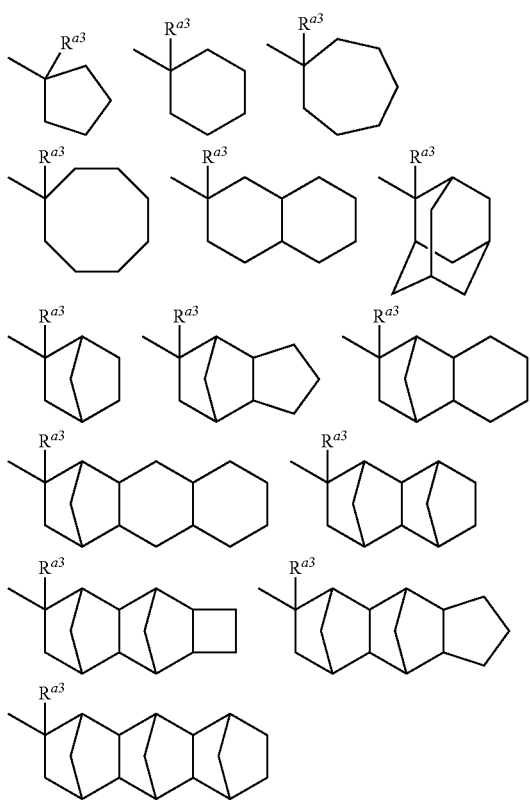

wherein $R^{a3}$ is the same as defined above.

The group represented by the formula (10) wherein $R^{a1}$, $R^{a2}$ and $R^{a3}$ independently each represent a C1-C8 alkyl group such as a tert-butyl group, the group represented by the formula (10) wherein $R^{a1}$ and $R^{a2}$ are bonded each other to form an adamantyl ring and $R^{a3}$ is a C1-C8 alkyl group such as a 2-alkyl-2-adamantyl group, and the group represented by the formula (10) wherein $R^{a1}$ and $R^{a2}$ are C1-C8 alkyl groups and $R^{a3}$ is an adamantyl group such as a 1-(1-adamantyl)-1-alkylalkoxycarbonyl group are preferable.

The structural unit having an acid-labile group is derived from a monomer having an acid-labile group in its side chain and a carbon-carbon double bond, and an acrylate monomer having an acid-labile group in its side chain or a methacryalte monomer having an acid-labile group in its side chain is preferable.

Preferable examples of the monomer include a 2-alkyl-2-adamantyl acrylate, a 2-alkyl-2-adamantyl methacrylate, 1-(1-adamantyl)-1-alkylalkyl acrylate, a 1-(1-adamantyl)-1-alkylalkylmethacrylate, a 2-alkyl-2-adamantyl 5-norbornene-2-carboxylate, a 1-(1-adamantyl)-1-alkylalkyl 5-norbornene-2-carboxylate, a 2-alkyl-2-adamantyl α-chloroacrylate and a 1-(1-adamantyl)-1-alkylalkyl α-chloroacrylate. Particularly when the 2-alkyl-2-adamantyl acrylate or the 2-alkyl-2-adamantyl methacrylate is used as the monomer for the resin component in the photoresist composition, a photoresist composition having excellent resolution tend to be obtained. Typical examples thereof include 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate, 2-isopropyl-2-adamantyl methacrylate, 2-n-butyl-2-adamantyl acrylate, 2-methyl-2-adamantyl α-chloroacrylate and 2-ethyl-2-adamantyl α-chloroacrylate. When particularly 2-ethyl-2-adamantyl acrylate, 2-ethyl-2-adamantyl methacrylate, 2-isopropyl-2-adamantyl acrylate or 2-isopropyl-2-adamantyl methacrylate is used for the photoresist composition, a photoresist composition having excellent sensitivity and heat resistance tends to be obtained.

The 2-alkyl-2-adamantyl acrylate can be usually produced by reacting a 2-alkyl-2-adamantanol or a metal salt thereof with an acrylic halide, and the 2-alkyl-2-adamantyl methacrylate can be usually produced by reacting a 2-alkyl-2-adamantanol or a metal salt thereof with a methacrylic halide.

Two or more kinds of monomers having a group or groups dissociated by the action of the acid may be used together, if necessary.

The content of the structural unit having an acid-labile group in the resin is usually 10 to 80% by mole based on total molar of all the structural units of the resin.

The resin preferably contains one or more structural units having one or more highly polar substituents. Examples of the structural unit having one or more highly polar substituents include a structural unit having a hydrocarbon group having at least one selected from the group consisting of a hydroxyl group, a cyano group, a nitro group and an amino group and a structural unit having a hydrocarbon group having one or more —CO—O—, —CO—, —O—, —SO$_2$— or —S—. A structural unit having a saturated cyclic hydrocarbon group having a cyano group or a hydroxyl group, a structural unit having a saturated cyclic hydrocarbon group in which one or more —CH$_2$— replaced by —O— or —CO—, and a structural unit having a lactone structure in its side chain are preferable, and a structural unit having a bridged hydrocarbon group having one or more hydroxyl groups, and a structural unit having a bridged hydrocarbon group having —CO—O— or —CO— are more preferable. Examples thereof include a structural unit derived from 2-norbornene having one or more hydroxyl groups, a structural unit derived from acrylonitrile or methacrylonitrile, a structural unit derived from hydroxyl-containing adamantyl acrylate or hydroxyl-containing adamantyl methacrylate, a structural unit derived from styrene monomer such as p-hydroxystyrene and m-hydroxystyrene, a structural unit derived from a structural unit derived from 1-adamantyl acrylate or 1-adamantyl methacrylate, and a structural unit derived from acryloyloxy-γ-butyrolactone or methacryloyloxy-γ-butyrolactone having a lactone ring which may have an alkyl group.

Specific examples of the structural unit derived from hydroxyl-containing adamantyl acrylate or hydroxyl-containing adamantyl methacrylate include a structural unit derived from 3-hydroxy-1-adamantyl acrylate; a structural unit derived from 3-hydroxy-1-adamantyl methacrylate; a structural unit derived from 3,5-dihydroxy-1-adamantyl acrylate; and a structural unit derived from 3,5-dihydroxy-1-adamantyl methacrylate.

3-Hydroxy-1-adamantyl acrylate, 3-hydroxy-1-adamantyl methacrylate, 3,5-dihydroxy-1-adamantyl acrylate and 3,5-dihydroxy-1-adamantyl methacrylate can be produced, for example, by reacting corresponding hydroxyadamantane with acrylic acid, methacrylic acid or its acid halide, and they are also commercially available.

When the resin has a structural unit derived from hydroxyl-containing adamantyl acrylate or hydroxyl-containing adamantyl methacrylate, the content thereof is preferably 5 to 50% by mole based on 100% by mole of all the structural units of the resin.

Examples of the structural unit derived from a monomer having a lactone ring which may have an alkyl group include a structural unit derived from acryloyloxy-γ-butyrolactone, a structural unit derived from methacryloyloxy-γ-butyrolactone and structural units represented by the formulae (a) and (b):

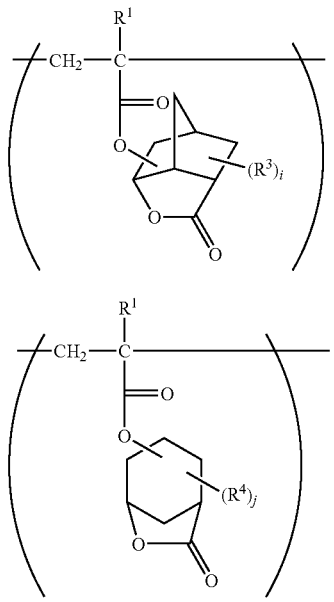

wherein $R^1$ and $R^2$ independently each represents a hydrogen atom or a methyl group, $R^3$ and $R^4$ are independently in each occurrence a hydrogen atom, a methyl group, a trifluoromethyl group or a halogen atom, and i and j independently each represents an integer of 1 to 3.

Further, the acryloyloxy-γ-butyrolactone and the methacryloyloxy-γ-butyrolactone can be produced by reacting corresponding α- or β-bromo-γ-butyrolactone with acrylic acid or methacrylic acid, or reacting corresponding α- or β-hydroxy-γ-butyrolactone with the acrylic halide or the methacrylic halide.

Examples of the monomers giving structural units represented by the formulae (a) and (b) include an acrylate of alicyclic lactones and a methacrylate of alicyclic lactones having the hydroxyl group described below, and mixtures thereof. These esters can be produced, for example, by reacting the corresponding alicyclic lactone having the hydroxyl group with acrylic acid or methacrylic acid, and the production method thereof is described in, for example, JP 2000-26446 A.

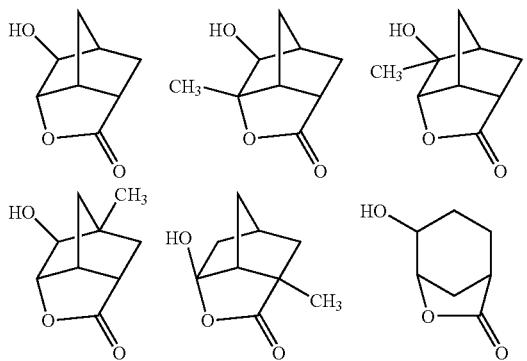

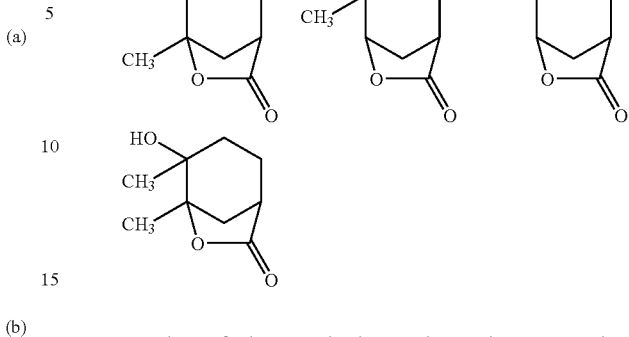

Examples of the acryloyloxy-γ-butyrolactone and the methacryloyloxy-γ-butyrolactone in which lactone ring may be substituted with the alkyl group include α-acryloyloxy-γ-butyrolactone, α-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-γ-butyrolactone, β-methacryloyloxy-γ-butyrolactone and β-methacryloyloxy-α-methyl-γ-butyrolactone.

When the resin has a structural unit derived from a monomer having a lactone ring which may have an alkyl group, the content thereof is preferably 5 to 50% by mole based on 100% by mole of all the structural units of the resin.

Among them, the structural unit derived from 3-hydroxy-1-adamantyl acrylate, the structural unit derived from 3-hydroxy-1-adamantyl methacrylate, the structural unit derived from 3,5-dihydroxy-1-adamantyl acrylate, the structural unit derived from 3,5-dihydroxy-1-adamantyl methacrylate, the structural unit derived from α-acryloyloxy-γ-butyrolactone, the structural unit derived from α-methacryloyloxy-γ-butyrolactone, the structural unit derived from β-acryloyloxy-γ-butyrolactone, the structural unit derived from β-methacryloyloxy-γ-butyrolactone, the structural unit represented by the formula (a) and the structural unit represented by the formula (b) are preferable, because a photoresist composition having good resolution and adhesiveness of photoresist to a substrate tends to be obtained.

When the exposing is conducted using KrF excimer laser, the resin preferably has a structural unit derived from a styrene monomer such as p-hydroxystyrene and m-hydroxystyrene, and the content thereof is preferably 5 to 90% by mole based on 100% by mole of all the structural units of the resin.

The resin can contain the other structural unit or units. Examples thereof include a structural unit derived from acrylic acid or methacrylic acid, a structural unit derived from an alicyclic compound having an olefinic double bond such as a structural unit represented by the formula (c):

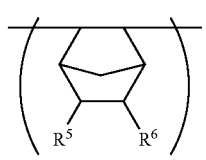

wherein $R^5$ and $R^6$ each independently represents a hydrogen atom, a C1-C3 alkyl group, a carboxyl group, a cyano group or a —COOU group in which U represents an alcohol residue, or R⁵ and R⁶ can be bonded together to form a carboxylic anhydride residue represented by —C(=O)OC(=O)—, a structural unit derived from an aliphatic unsaturated dicarboxylic anhydride such as a structural unit represented by the formula (d):

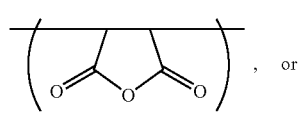

a structural unit represented by the formula (e):

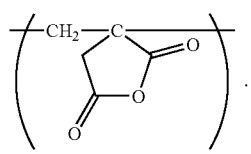

In $R^5$ and $R^6$, examples of the C1-C3 alkyl group include a methyl group, an ethyl group, a propyl group and an isopropyl group. The —COOU group is an ester formed from the carboxyl group, and examples of the alcohol residue corresponding to U include an optionally substituted C1-C8 alkyl group, 2-oxooxolan-3-yl group and 2-oxooxolan-4-yl group, and examples of the substituent on the C1-C8 alkyl group include a hydroxyl group and an alicyclic hydrocarbon group.

Specific examples of the monomer giving the structural unit represented by the above-mentioned formula (c) may include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When U in the —COOU group is the acid-labile group, the structural unit represented by the formula (c) is a structural unit having the acid-labile group even if it has the norbornane structure. Examples of monomers giving a structural unit having the acid-labile group include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl)ethyl 5-norbornene-2-carboxylate and 1-(1-adamantyl)-1-methylethyl 5-norbornene-2-carboxylate.

The resin can be obtained by conducting polymerization reaction of a monomer or monomers having the acid-labile group and an olefinic double bond. The polymerization reaction is usually carried out in the presence of a radical initiator. This polymerization reaction can be conducted according to known methods.

The resin usually has 10,000 or more of the weight-average molecular weight, preferably 10,500 or more of the weight-average molecular weight, more preferably 11,000 or more of the weight-average molecular weight, much more preferably 11,500 or more of the weight-average molecular weight, and especially preferably 12,000 or more of the weight-average molecular weight. When the weight-average molecular weight of the resin is too large, defect of the photoresist film tends to generate, and therefore, the resin preferably has 40,000 or less of the weight-average molecular weight, more preferably 39,000 or less of the weight-average molecular weight, much more preferably 38,000 or less of the weight-average molecular weight, and especially preferably 37,000 or less of the weight-average molecular weight. The weight-average molecular weight can be measured with gel permeation chromatography.

The present resist composition preferably includes 80 to 99.9% by weight of the resin component and 0.1 to 20% by weight of the acid generator component based on sum of the resin component and the acid generator component. Herein, "acid generator component" means the salt having a group containing a group represented by the formula (I) and the other acid generator(s) contained in the photoresist composition.

In the present resist composition, performance deterioration caused by inactivation of acid which occurs due to post exposure delay can be diminished by adding an organic base compound, particularly a nitrogen-containing organic base compound as a quencher.

Specific examples of the nitrogen-containing organic base compound include an amine compound represented by the following formulae:

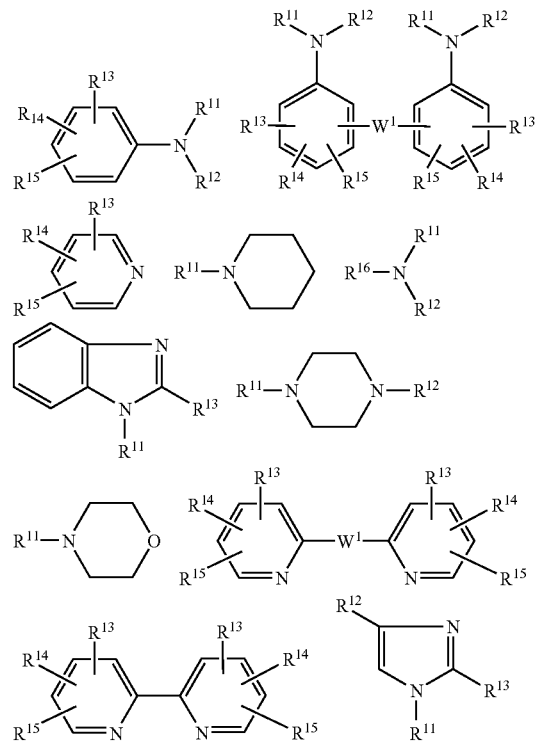

wherein $R^{11}$ and $R^{12}$ independently represent a hydrogen atom, a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group which may be substituted with a C1-C6 alkoxy group, $R^{13}$ and $R^{14}$ independently represent a hydrogen atom, a C1-C6 alkyl group, a C5-C10 cycloalkyl group, a C6-C10 aryl group or a C1-C6 alkoxy group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, or $R^{13}$ and $R^{14}$ bond together with the carbon atoms to which they bond to form an aromatic ring, $R^{15}$ represent a hydrogen atom, a C1-C6 alkyl group, a C5-C10 cycloalkyl group, a C6-C10 aryl group, a C1-C6 alkoxy group or a nitro group, and the alkyl, cycloalkyl, aryl and alkoxy groups may be substituted with at least one group selected from the group consisting of a hydroxyl group, an amino group which may be substituted with a C1-C4 alkyl group and a C1-C6 alkoxy group, $R^{16}$ represents a C1-C6 alkyl group or a C5-C10 cycloalkyl group, and the alkyl and cycloalkyl groups may be substituted with at least one group selected from the group consisting of a hydroxyl group, an amino group which may be substituted with a C1-C4 alkyl group and a C1-C6 alkoxy group, and $W^1$ represents —CO—, —NH—, —S—, —S—S—, an C2-C6 alkylene group, and a quaternary ammonium hydroxide represented by the following formula:

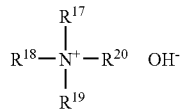

wherein $R^{17}$, $R^{18}$, $R^{19}$ and $R^{20}$ independently represent a C1-C6 alkyl group, a C5-C10 cycloalkyl group or a C6-C10 aryl group, and the alkyl, cycloalkyl and aryl groups may be substituted with at least one group selected from the group consisting of a hydroxyl group, an amino group which may be substituted with a C1-C4 alkyl group and a C1-C6 alkoxy group.

Examples of the amino group which may be substituted with the C1-C4 alkyl group include an amino group, a methylamino group, an ethylamino group, a butylamino group, a dimethylamino group and a diethylamino group. Examples of the C1-C6 alkoxy group which may be substituted with the C1-C6 alkoxy group include a methoxy group, an ethoxy group, a propoxy group, an isopropoxy group, a butoxy group, a tert-butoxy group, a pentyloxy group, a hexyloxy group and a 2-methoxyethoxy group.

Specific examples of the C1-C6 alkyl group which may be substituted with at least one group selected from the group consisting of a hydroxyl group, an amino group which may be substituted with a C1-C4 alkyl group, and a C1-C6 alkoxy group which may be substituted with a C1-C6 alkoxy group include a methyl group, an ethyl group, a propyl group, an isopropyl group, a butyl group, a tert-butyl group, a pentyl group, a hexyl group, a 2-(2-methoxyethoxy)ethyl group, a 2-hydroxyethyl group, a 2-hydroxypropyl group, a 2-aminoethyl group, a 4-aminobutyl group and a 6-aminohexyl group.

Specific examples of the C5-C10 cycloalkyl group which may be substituted with at least one group selected from the group consisting of a hydroxyl group, an amino group which may be substituted with a C1-C4 alkyl group and a C1-C6 alkoxy group include a cyclopentyl group, a cyclohexyl group, a cycloheptyl group and a cyclooctyl group.

Specific examples of the C6-C10 aryl group which may be substituted with at least one group selected from the group consisting of a hydroxyl group, an amino group which may be substituted with a C1-C4 alkyl group or a C1-C6 alkoxy group include a phenyl group and a naphthyl group.

Specific examples of the C1-C6 alkoxy group include a methoxy group, an ethoxy group, a propoxy group, an isopropoxy group, a butoxy group, a tert-butoxy group, a pentyloxy group and a hexyloxy group.

Specific examples of the C2-C6 alkylene group include an ethylene group, a trimethylene group and a tetramethylene group.

Specific examples of the amine compound include hexylamine, heptylamine, octylamine, nonylamine, decylamine, aniline, 2-methylaniline, 3-methylaniline, 4-methylaniline, 4-nitroaniline, 1-naphthylamine, 2-naphthylamine, ethylenediamine, tetramethylenediamine, hexamethylenediamine, 4,4'-diamino-1,2-diphenylethane, 4,4'-diamino-3,3'-dimethyldiphenylmethane, 4,4'-diamino-3,3'-diethyldiphenylmethane, dibutylamine, dipentylamine, dihexylamine, diheptylamine, dioctylamine, dinonylamine, didecylamine, N-methylaniline, piperidine, diphenylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethyldiheptylamine, ethyldioctylamine, ethyldinonylamine, ethyldidecylamine, dicyclohexylmethylamine, tris[2-(2-methoxyethoxy)ethyl]amine, triisopropanolamine, N,N-dimethylaniline, 2,6-diisopropylaniline, imidazole, benzimidazole, pyridine, 4-methylpyridine, 4-methylimidazole, bipyridine, 2,2'-dipyridylamine, di-2-pyridyl ketone, 1,2-di(2-pyridyl)ethane, 1,2-di(4-pyridyl)ethane, 1,3-di(4-pyridyl)propane, 1,2-bis(2-pyridyl)ethylene, 1,2-bis(4-pyridyl)ethylene, 1,2-bis(4-pyridyloxy)ethane, 4,4'-dipyridyl sulfide, 4,4'-dipyridyl disulfide, 1,2-bis(4-pyridyl)ethylene, 2,2'-dipicolylamine and 3,3'-dipicolylamine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

A hindered amine compound having a piperidine skeleton as disclosed in JP 11-52575 A1 can be also used as the quencher.

In the point of forming patterns having higher resolution, the quaternary ammonium hydroxide is preferably used as the quencher.

When the basic compound is used as the quencher, the present resist composition preferably includes 0.01 to 1% by weight of the basic compound based on the total amount of the resin component and the acid generator component.

The present resist composition can contain, if necessary, a small amount of various additives such as a sensitizer, a dissolution inhibitor, other polymers, a surfactant, a stabilizer and a dye as long as the effect of the present invention is not prevented.

The present resist composition is usually in the form of a resist liquid composition in which the above-mentioned ingredients are dissolved in a solvent and the resist liquid composition is applied onto a substrate such as a silicon wafer by a conventional process such as spin coating. The solvent used is sufficient to dissolve the above-mentioned ingredients, have an adequate drying rate, and give a uniform and smooth coat after evaporation of the solvent. Solvents generally used in the art can be used.

Examples of the solvent include a glycol ether ester such as ethyl cellosolve acetate, methyl cellosolve acetate and propylene glycol monomethyl ether acetate; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone. These solvents may be used alone and two or more thereof may be mixed to use.

A photoresist pattern can be produced by the following steps (1) to (5):

(1) a step of applying the photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column (Three Columns with guard column): TSKgel Multipore HXL-M, manufactured by TOSOH CORPORATION, Solvent: Tetrahydrofuran, Flow rate: 1.0 mL/min., Detector: RI detector, Column temperature: 40° C., Injection volume: 100 μL] using polystyrene as a standard reference material. Structures of compounds were determined by NMR (GX-270 Type or EX-270 Type, manufactured by JEOL LTD.) and mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

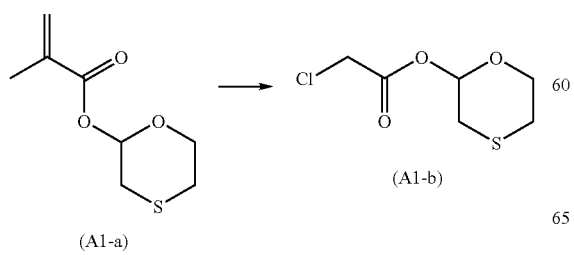

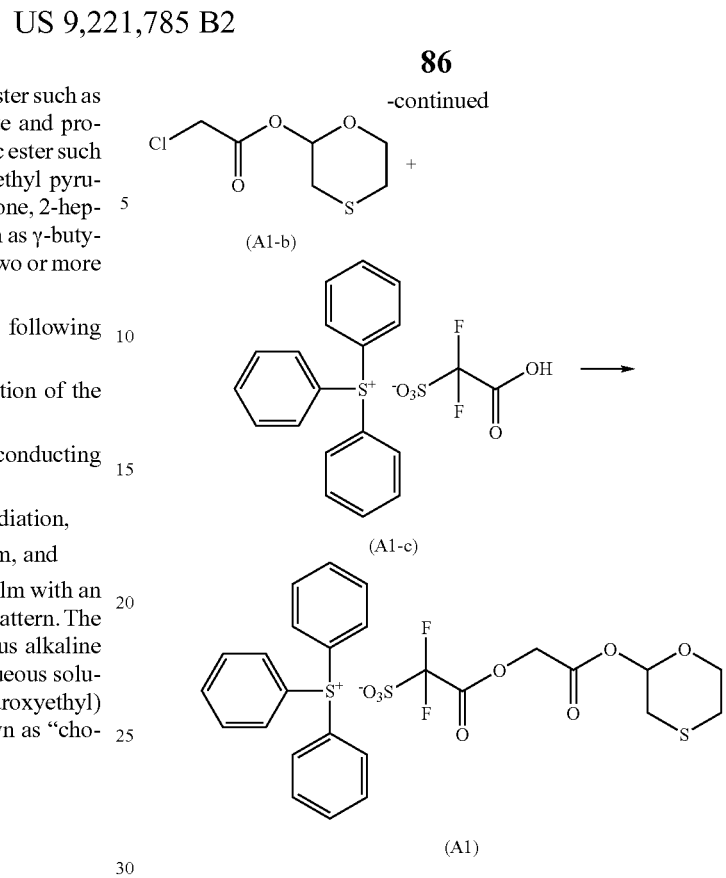

To a mixture of 7.79 parts of a compound represented by the formula (A1-a) and 25.00 parts of dimethylsulfoxide, 1.50 parts of 10% hydrochloric acid was added dropwise over 30 minutes at 23° C. with stirring. The obtained mixture was stirred at 20° C. for 8 hours. To the mixture, 10.00 parts of aqueous saturated sodium hydrogen carbonate solution and 50.00 parts of ethyl acetate were added, and the obtained mixture was stirred followed by conducting separation. The obtained organic layer was washed with 20.00 parts of ion-exchanged water. This washing was repeated three times. The obtained organic layer was concentrated. The obtained residue was mixed with 25.00 parts of tetrahydrofuran and the obtained mixture was stirred at 23° C. for 30 minutes. To the mixture, 3.24 parts of pyridine was added and the resultant mixture was heated at 30° C. To the mixture, a solution prepared by dissolving 5.29 parts of chloroacetyl chloride in 25.00 parts of tetrahydrofuran was added dropwise over 30 minutes, and then, the obtained mixture was stirred at 23° C. for 8 hours. The resultant mixture was cooled down to 5° C., and 50 parts of ion-exchanged water and 100 parts of ethyl acetate, which were cooled at 5° C., were added thereto followed by conducting separation. The obtained organic layer was washed with 30 parts of ion-exchanged water and this washing was repeated three times. The obtained organic layer was concentrated and dried to obtain 0.92 part of a compound represented by the formula (A1-b).

A mixture of 0.59 parts of the compound represented by the formula (A1-b) and 10.00 parts of N,N-dimethylformamide was stirred at 23° C. for 30 minutes. To the obtained mixture, 0.21 part of potassium carbonate and 0.06 part of potassium iodide were added, and the obtained mixture was stirred at 30° C. for 4 hours. To the obtained mixture, a solution prepared by dissolving 1.32 parts of a compound represented by the formula (A1-c) in 10.00 parts of N,N-dimethylformamide was added over 30 minutes, and the resultant mixture was stirred at 30° C. for 6 hours. The obtained mixture was cooled to room temperature, and 20.00 parts of ion-exchanged water and 40.00 parts of ethyl acetate were added thereto. The obtained mixture was separated to obtain an organic layer. The organic layer was washed with 20.00 parts of 5% aqueous potassium carbonate solution and then, washed with 20.00 parts of ion-exchanged water. This washing was repeated three times. The organic layer was mixed with 1 parts of magnesium sulfate and then, the resultant mixture was stirred and filtrated. The filtrate was concentrated, and the obtained residue was dissolved in 5.00 parts of acetonitrile. The obtained solution was concentrated, and the obtained residue was mixed with 5.00 parts of ethyl acetate and the supernatant solution was removed. The obtained residue was mixed with 5.00 parts of tert-butyl methyl ether and supernatant solution was removed. The obtained residue was dissolved in chloroform, and the obtained solution was concentrated to obtain 0.31 part of a salt represented by the above-mentioned formula (A1) in the form of orange-colored oil. This is called as acid generator A1. This is called as acid generator A1.

MS (ESI(+) Spectrum): $M^+$ 263.1

MS (ESI(−) Spectrum): $M^-$ 335.0

$^1$H-NMR (dimethylsulfoxide-$d_6$, Internal Standard: tetramethylsilane): δ (ppm) 2.49-2.68 (m, 3H), 2.83-2.90 (m, 1H), 3.77-3.86 (m, 1H), 4.07-4.16 (m, 3H), 5.83 (m, 1H), 7.70-7.90 (m, 15H)

Example 2

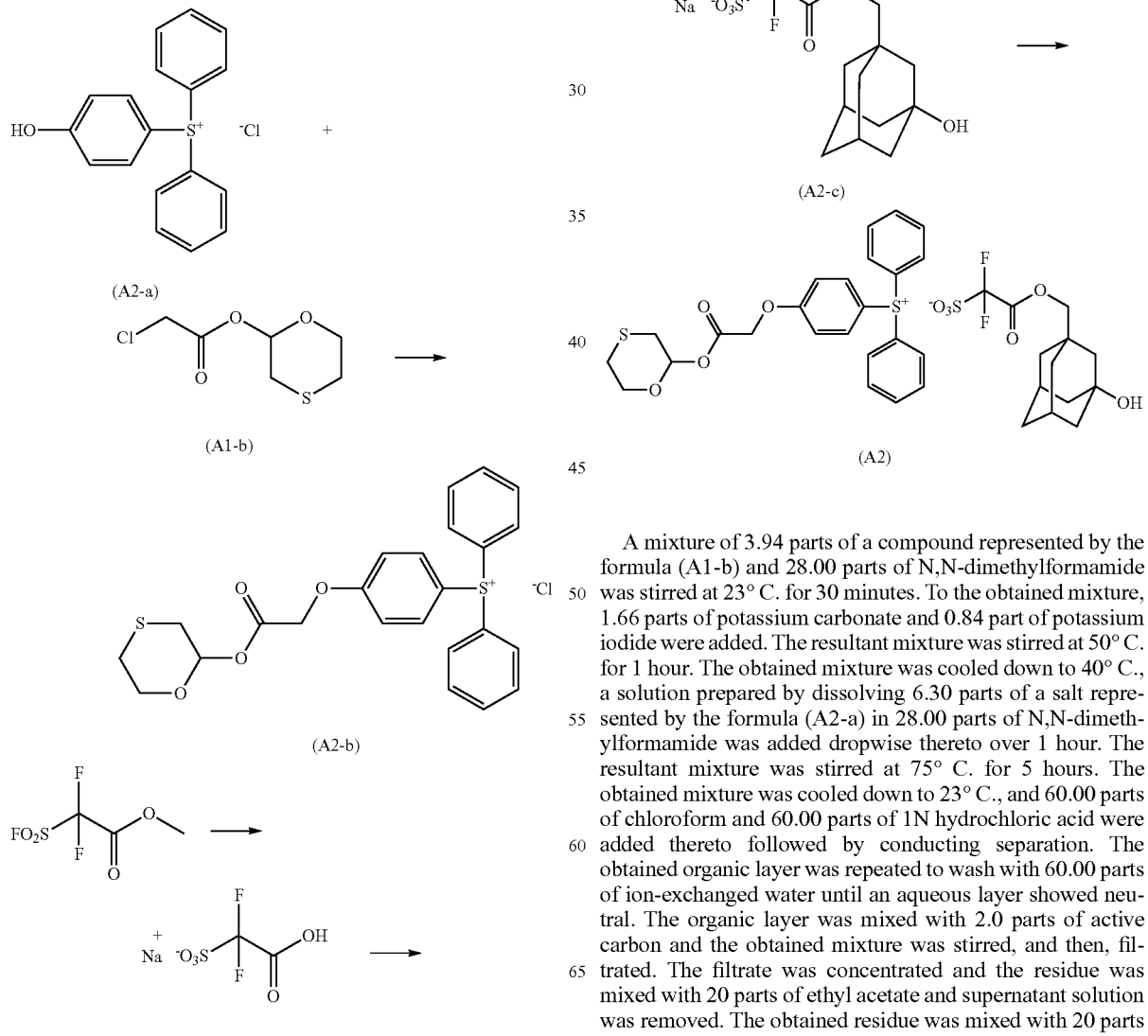

A mixture of 3.94 parts of a compound represented by the formula (A1-b) and 28.00 parts of N,N-dimethylformamide was stirred at 23° C. for 30 minutes. To the obtained mixture, 1.66 parts of potassium carbonate and 0.84 part of potassium iodide were added. The resultant mixture was stirred at 50° C. for 1 hour. The obtained mixture was cooled down to 40° C., a solution prepared by dissolving 6.30 parts of a salt represented by the formula (A2-a) in 28.00 parts of N,N-dimethylformamide was added dropwise thereto over 1 hour. The resultant mixture was stirred at 75° C. for 5 hours. The obtained mixture was cooled down to 23° C., and 60.00 parts of chloroform and 60.00 parts of 1N hydrochloric acid were added thereto followed by conducting separation. The obtained organic layer was repeated to wash with 60.00 parts of ion-exchanged water until an aqueous layer showed neutral. The organic layer was mixed with 2.0 parts of active carbon and the obtained mixture was stirred, and then, filtrated. The filtrate was concentrated and the residue was mixed with 20 parts of ethyl acetate and supernatant solution was removed. The obtained residue was mixed with 20 parts of methyl tert-butyl ether, and supernatant solution was removed. The obtained residue was dissolved in chloroform, and the obtained solution was concentrated to obtain 3.88 parts of a salt represented by the above-mentioned formula (A2-b).

Into a mixture of 100 parts of methyl difluoro(fluorosulfonyl)acetate and 150 parts of ion-exchanged water, 230 parts of 30% aqueous sodium hydroxide solution was added dropwise in an ice bath. The resultant mixture was heated and refluxed at 100° C. for 3 hours. After cooling down to room temperature, the cooled mixture was neutralized with 88 parts of concentrated hydrochloric acid and the solution obtained was concentrated to obtain 164.4 parts of sodium salt of difluorosulfoacetic acid (containing inorganic salt, purity: 62.7%).

To a mixture of 1.9 parts of sodium salt of difluorosulfoacetic acid (purity: 62.7%) and 9.5 parts of N,N-dimethylformamide, 1.0 part of 1,1'-carbonyldiimidazole was added and the resultant solution was stirred for 2 hours. The solution was added to a solution prepared by mixing 1.1 parts of 3-hydroxyadamantanemethanol, 5.5 parts of N,N-dimethylformamide and 0.2 part of sodium hydride and stirring for 2 hours. The resultant solution was stirred for 15 hours to obtain a solution containing the salt represented by the above-mentioned formula (A2-c).

To the solution containing 1.81 parts of the salt represented by the above-mentioned formula (A2-c), 3.2 parts of chloroform and 2.38 parts of the salt represented by the formula (A2-b) were added. The resultant mixture was stirred for 15 hours, and then, washed with ion-exchanged water. To the obtained solution, 1.0 part of active carbon was added and the resultant mixture was stirred followed by filtration. The filtrate was concentrated and the obtained residue was mixed with 10 parts of ethyl acetate and supernatant solution was removed. The obtained residue was mixed with 10 parts of methyl tert-butyl ether and supernatant solution was removed. The obtained residue was dissolved in chloroform and the resultant solution was concentrated to obtain 1.48 parts of a salt represented by the formula (A2). This is called as acid generator A2.

MS (ESI(+) Spectrum): M⁺ 439.1
MS (ESI(−) Spectrum): M⁻ 339.1
$^1$H-NMR (dimethylsulfoxide-$d_6$, Internal Standard: tetramethylsilane): δ (ppm) 1.35-1.80 (m, 12H), 2.10 (s, 2H), 2.45-2.70 (m, 3H), 2.82-2.95 (m, 1H), 3.75-3.89 (m, 3H), 4.08-4.19 (m, 1H), 4.40-4.42 (s, 1H), 4.96 (s, 2H), 5.85-5.92 (m, 1H), 7.28-7.35 (m, 2H), 7.70-7.90 (m, 12H)

Resin Synthesis Example 1

Monomers used in this Example are following monomers B, C, D, E and F.

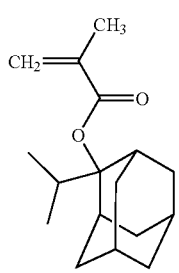

E

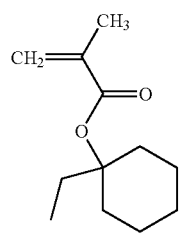

F

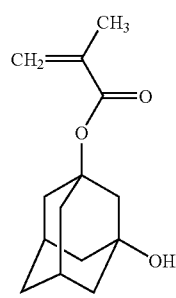

B

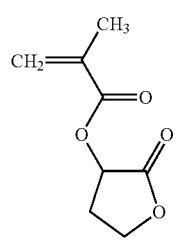

C

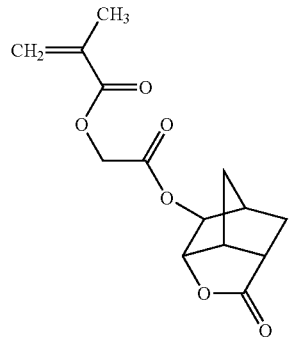

D

The monomers E, F, B, C and D were mixed in a molar ratio of 30/14/6/20/30 (monomer E/monomer F/monomer B/monomer C/monomer D), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a mixture of a large amount of methanol and water (methanol/water volume ratio=4/1) to cause precipitation, and this operation was repeated three times for purification. As a result, a resin having a weight-average molecular weight of about $8.1 \times 10^3$ was obtained in a yield of 65%. The resin had the following structural units. This is called as resin B1.

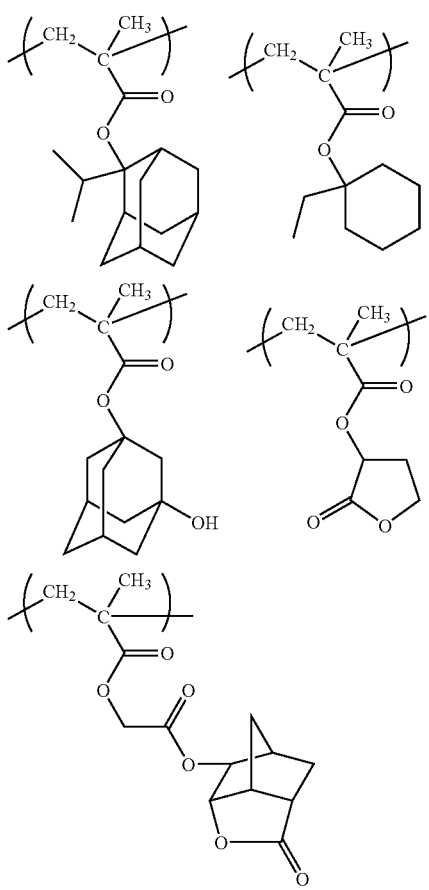

Resin Synthesis Example 2

Monomers used in this Example are following monomers A, B and C.

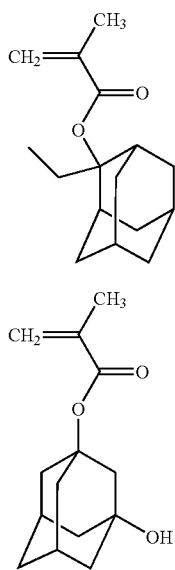

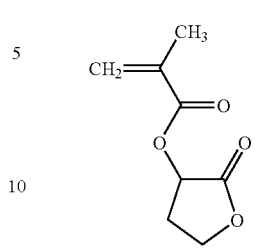

The monomers A, B and C were mixed in a molar ratio of 50/25/25 (monomer A/monomer B/monomer C), and 1,4-dioxane in 1.5 times part based on total parts of all monomers was added to prepare a mixture. To the mixture, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 80° C. for about 6 hours. The reaction mixture obtained was poured into a mixture of a large amount of methanol and water (methanol/water volume ratio=about 3/1) to cause precipitation, and this operation was repeated three times for purification. As a result, a resin having a weight-average molecular weight of about $9.2 \times 10^3$ was obtained in a yield of 60%. The resin had the following structural units. This is called as resin B2.

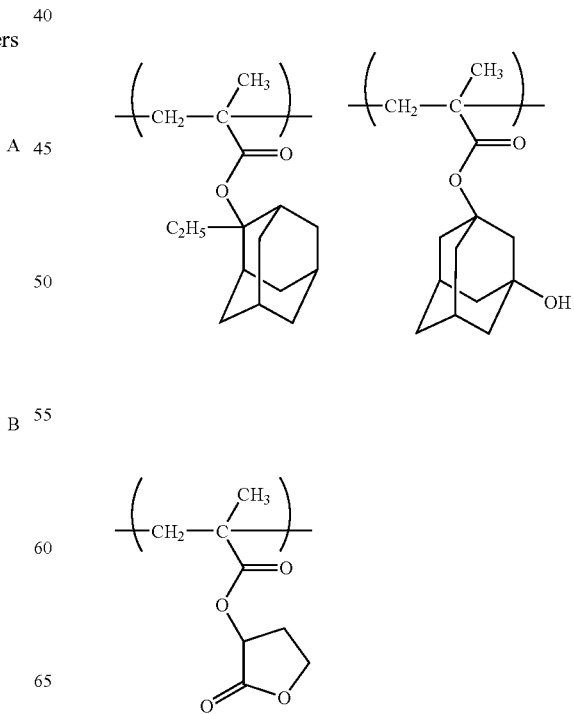

Examples 3 to 8 and Comparative Example 1

Acid Generator

Salt A1, A2, C1
C1:

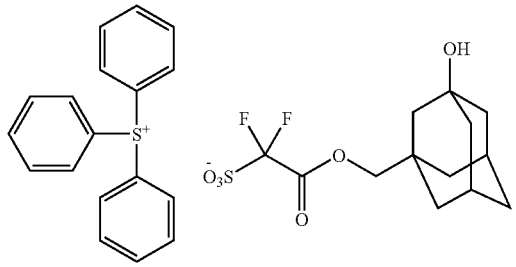

Resin

Resin B1, B2

Quencher

Q1: 2,6-diisopropylaniline

Solvent

| Y1: | propylene glycol monomethyl ether acetate | 265 parts |
|---|---|---|
| | 2-heptanone | 20 parts |
| | propylene glycol monomethyl ether | 20 parts |
| | γ-butyrolactone | 3.5 parts |

The following components were mixed and dissolved, further, filtrated through a fluorine resin filter having pore diameter of 0.2 to prepare photoresist compositions.
Resin (kind and amount are described in Table 1)
Acid generator (kind and amount are described in Table 1)
Quencher (kind and amount are described in Table 1)
Solvent (kind is described in Table 1)

TABLE 1

| Ex. No. | Resin (kind/amount (part)) | Acid generator (kind/amount (part)) | Quencher (kind/amount (part)) | Solvent |
|---|---|---|---|---|
| Ex. 3 | B1/10 | A1/0.7 | Q1/0.065 | Y1 |
| Ex. 4 | B1/10 | A1/0.4 C1/0.3 | Q1/0.065 | Y1 |
| Ex. 5 | B2/10 | A1/0.7 | Q1/0.065 | Y1 |
| Ex. 6 | B1/10 | A2/0.7 | Q1/0.065 | Y1 |
| Ex. 7 | B1/10 | A2/0.4 C1/0.3 | Q1/0.065 | Y1 |
| Ex. 8 | B2/10 | A2/0.7 | Q1/0.065 | Y1 |
| Comp. Ex. 1 | B2/10 | C1/0.7 | Q1/0.065 | Y1 |

Silicon wafers were each coated with "ARC-29", which is an organic anti-reflective coating composition available from Nissan Chemical Industries, Ltd., and then baked at 205° C. for 60 seconds, to form a 78 nm-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at 100° C. for 60 seconds. Using an ArF excimer stepper ("FPA-5000AS3" manufactured by CANON INC., NA=0.75, 2/3 Annular), each wafer thus formed with the respective resist film was subjected to line and space pattern exposure, with the exposure quantity being varied stepwise.

After the exposure, each wafer was subjected to post-exposure baking on a hotplate at 100° C. for 60 seconds and then to paddle development for 60 seconds with an aqueous solution of 2.38 wt % tetramethylammonium hydroxide.

Each of a dark field pattern developed on the organic anti-reflective coating substrate after the development was observed with a scanning electron microscope, the results of which are shown in Table 2. The term "dark field pattern", as used herein, means a pattern obtained by exposure and development through a reticle comprising chromium base surface (light-shielding portion) and linear glass layers (light-transmitting portion) formed in the chromium surface and aligned with each other. Thus, the dark field pattern is such that, after exposure and development, resist layer surrounding the line and space pattern remains on substrate.

Resolution: The photoresist pattern at the exposure dose that the line pattern and the space pattern become 1:1 after exposure through 100 nm line and space pattern mask and development was observed with a scanning electron microscope. When 85 nm line and space pattern was resolved, the resolution is good and its evaluation is marked by "○", and when 85 nm line and space pattern was not resolved or was resolved but the toppling of the patterns was observed, the resolution is bad and its evaluation is marked by "x".

Line Edge Roughness (LER): The photoresist pattern was observed with a scanning electron microscope, and the difference between the height of the highest point and height of the lowest point of the scabrous wall surface of the photoresist pattern was measured. When the difference is 8 nm or less, LER is good and its evaluation is marked by "○", and when the difference is more than 8 nm, LER is bad and its evaluation is marked by "x". The smaller the difference is, the better the pattern is.

TABLE 2

| Ex. No. | Resolution | LER |
|---|---|---|
| Ex. 3 | ○ | ○ |
| Ex. 4 | ○ | ○ |
| Ex. 5 | ○ | ○ |
| Ex. 6 | ○ | ○ |
| Ex. 7 | ○ | ○ |
| Ex. 8 | ○ | ○ |
| Comp. Ex. 1 | X | X |

The salt of the present invention is novel and is useful as an acid generator, and the photoresist composition containing the salt of the present invention provides a photoresist pattern having good resolution and good LER, and is especially suitable for ArF excimer laser lithography, KrF excimer laser lithography, ArF immersion lithography and EUV immersion lithography.

What is claimed is:

1. A salt having a group represented by the formula (I-1):

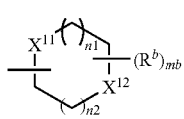
(I-1)

wherein $X^{11}$ and $X^{12}$ independently each represent an unsubstituted divalent oxygen atom or an unsubstituted divalent sulfur atom, $R^b$ is independently in each occurrence a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, mb represents an integer of 0 to 4, n1 represents 1 or 2, and n2 represents 0 or 1.

2. The salt according to claim 1, wherein the group represented by the formula (I-1) is a group represented by the formula (I-2):

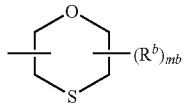
(I-2)

wherein $R^b$ is independently in each occurrence a halogen atom, a hydroxyl group, a C1-C12 alkyl group, a C1-C12 alkoxy group, a C6-C12 aryl group, a C7-C12 aralkyl group, a glycidyloxy group or a C2-C4 acyl group, and mb represents an integer of 0 to 4.

3. The salt according to claim 1, wherein the salt is represented by the formula (b1):

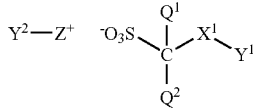
(b1)

wherein $Q^1$ and $Q^2$ each independently represent a fluorine atom or a C1-C6 perfluoroalkyl group, $X^1$ represents a C1-C17 saturated hydrocarbon group which can have one or more substituents, and one or more methylene groups in the saturated hydrocarbon group can be replaced by —O— or —CO—, $Y^1$ represents a C3-C36 alicyclic hydrocarbon group, a C6-C24 aromatic hydrocarbon group or a group represented by the formula (I-1), Z represents an organic group, and $Y^2$ represents a hydrogen atom or a group containing the group represented by the formula (I-1), provided that at least one of $Y^1$ and $Y^2$ has the group represented by the formula (I-1).

4. A photoresist composition comprising the salt according to claim 1 and a resin comprising a structural unit having an acid-labile group and being insoluble or poorly soluble in an aqueous alkali solution but becoming soluble in an aqueous alkali solution by the action of an acid.

5. The photoresist composition according to claim 4, wherein the photoresist composition further contains a basic compound.

6. A process for producing a photoresist pattern comprising the following steps (1) to (5):

(1) a step of applying the photoresist composition according to claim 4 or 5 on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

* * * * *